United States Patent
Ball

(10) Patent No.: US 11,377,683 B2
(45) Date of Patent: Jul. 5, 2022

(54) LOOPED PRIMER AND LOOP-DE-LOOP METHOD FOR DETECTING TARGET NUCLEIC ACID

(71) Applicant: Uh-Oh Labs Inc., Santa Clara, CA (US)

(72) Inventor: Cameron Scott Ball, Sunnyvale, CA (US)

(73) Assignee: Uh-Oh Labs Inc., Santa Clara, CA (US)

( * ) Notice: Subject to any disclaimer, the term of this patent is extended or adjusted under 35 U.S.C. 154(b) by 0 days.

(21) Appl. No.: 17/200,519

(22) Filed: Mar. 12, 2021

(65) Prior Publication Data

US 2021/0285039 A1     Sep. 16, 2021

Related U.S. Application Data

(60) Provisional application No. 62/989,140, filed on Mar. 13, 2020.

(51) Int. Cl.
| | | |
|---|---|---|
| *C12Q 1/6853* | (2018.01) | |
| *C12Q 1/6818* | (2018.01) | |
| *C12Q 1/6825* | (2018.01) | |
| *C12Q 1/48* | (2006.01) | |

(52) U.S. Cl.
CPC ............ *C12Q 1/6853* (2013.01); *C12Q 1/48* (2013.01); *C12Q 1/6818* (2013.01); *C12Q 1/6825* (2013.01)

(58) Field of Classification Search
None
See application file for complete search history.

(56) References Cited

U.S. PATENT DOCUMENTS

| | | |
|---|---|---|
| 5,866,336 A | 2/1999 | Nazarenko et al. |
| 6,326,145 B1 | 12/2001 | Whitcombe et al. |
| 6,410,278 B1 | 6/2002 | Notomi et al. |
| 6,974,670 B2 | 12/2005 | Notomi et al. |
| 7,846,695 B2 | 12/2010 | Nagamine |
| 7,851,186 B2 | 12/2010 | Nagamine |
| 8,394,609 B2 | 3/2013 | Nazarenko et al. |
| 9,909,168 B2 | 3/2018 | Notomi et al. |
| 2002/0182620 A1 | 12/2002 | Patel et al. |
| 2014/0349295 A1 | 11/2014 | Hosaka et al. |
| 2016/0289752 A1 | 10/2016 | Bamford |

OTHER PUBLICATIONS

Thelwell, Mode of action and application of Scorpion primers to mutation detection, Nucleic Acids Res., 28(19): 3752-3761, 2000. (Year: 2000).*
Vet, Design and Optimization of Molecular Beacon Real-Time Polymerase Chain Reaction Assays, In: Herdewijn P. (eds) Oligonucleotide Synthesis. Methods in Molecular Biology, vol. 288. Humana Press, 2005. (Year: 2005).*
Nagamine, Accelerated reaction by loop-mediated isothermal amplification using loop primers, Molecular and Cellular Probes, 16, 223-229, 2002. (Year: 2002).*
Badolo, A. et al., "Detection of G119S ace-$1^R$ mutation in field-collected *Anopheles gambiae* mosquitoes using allele-specific loop-mediated isothermal amplification (AS-LAMP) method," Malaria Journal, 2015, eight pages, vol. 14, No. 477.
Ball, C. S. et al., "Quenching of Unincorporated Amplification Signal Reporters in Reverse-Transcription Loop-Mediated Isothermal Amplification Enabling Bright, Single-Step, Closed-Tube, and Multiplexed Detection of RNA Viruses," Analytical Chemistry, 2016, pp. 3562-3568, vol. 88.
Carlos, F. F. et al., "Allele specific LAMP-gold nanoparticle for characterization of single nucleotide polymorphisms," Biotechnology Reports, Dec. 2017, pp. 21-25, vol. 16.
Demczuk, W. et al., "Genomic Epidemiology and Molecular Resistance Mechanisms of Azithromycin-Resistant *Neisseria gonorrhoeae* in Canada from 1997 to 2014," Journal of Clinical Microbiology, May 2016, pp. 1304-1313, vol. 54, No. 5.
Edwards. T., et al., "Loop-Mediated Isothermal Amplification Test for Detection of *Neisseria gonorrhoeae* in Urine Samples and Tolerance of the Assay to the Presence of Urea," Journal of Clinical Microbiology, Jun. 2014, pp. 2163-2165, vol. 52, No. 6.
Elwell, C. et al., "*Chlamydia* cell biology and pathogenesis," Nature Review Microbiology, Jun. 2016, 36 pages, vol. 14, No. 6.
Engelen, W. et al., "Nucleic acid detection using BRET-beacons based on bioluminescent protein—DNA hybrids," Chem. Commun., Mar. 2017, pp. 2862-2865, vol. 53, No. 19.
Gadkar, V. J. et al., "Real-time Detection and Monitoring of Loop Mediated Amplification (LAMP) Reaction Using Self-quenching and De-quenching Fluorogenic Probes," Scientific Reports, Apr. 3, 2018, 10 pages.
Gandelman, O. A. et al., "Novel Bioluminescent Quantitative Detection of Nucleic Acid Amplification in Real-Time," PLoS ONE, Nov. 2010, 13 pages, vol. 5, No. 11, e14155.
Hosaka, N. et al., "Rapid detection of human immunodeficiency virus type 1 group M by a reverse transcription-loop-mediated isothermal amplification assay," Journal of Viroloeical Methods, 2009, pp. 195-199, vol. 157.
Huang, W., et al., "Comparative effectiveness of a rapid point-of-care test for detection of *Chlamydia trachomatis* among women in a clinical setting," Sexually Transmitted Infections, Mar. 2013, 14 pages, vol. 89, No. 2.
Jevtuševskaja, J. et al., "Combination with antimicrobial peptide lyses improves loop-mediated isothermal amplification based method for *Chlamydia trachomatis* detection directly in urine sample," BMC Infectious Diseases, 2016, eight pages, vol. 16, No. 329.
Jiang, H.-X. et al., "Real-time monitoring of rolling circle amplification using aggregation-induced emission: applications in biological detection," Chemical Communications, 2015, six pages, No. 10.1039/C5CC07340E.

(Continued)

*Primary Examiner* — Samuel C Woolwine
*Assistant Examiner* — Carolyn L Greene
(74) *Attorney, Agent, or Firm* — Fenwick & West LLP

(57) ABSTRACT

The present disclosure provides a novel loop-de-loop method of detecting a target nucleic acid using a biosensor-labeled oligonucleotide. Further provided herein is a looped primer and a kit for use in the method.

29 Claims, 25 Drawing Sheets
Specification includes a Sequence Listing.

(56) References Cited

OTHER PUBLICATIONS

Jiang, Y. S. et al., "Robust Strand Exchange Reactions for the Sequence-Specific, Real-Time Detection of Nucleic Acid Amplicons," Analytical Chemistry, 2015, pp. 3314-3320, vol. 87.

Kouguchi, Y. et al., "Homogenous, real-time duplex loop-mediated isothermal amplification using a single fluoropbore-labeled primer and an intercalator dye: Its application to the simultaneous detection of Shiga toxin genes 1 and 2 in Shiga toxigenic *Escherichia coli* isolates," Molecular and Cellular Probes, Aug. 2010, pp. 190-195, vol. 24, No. 4.

Kubota, R. et al., "FRET-Based Assimilating Probe for Sequence-Specific Real-Time Monitoring of Loop-Mediated Isothermal Amplification (LAMP)," Biological Engineering Transactions, 2011, pp. 81-100, vol. 4, No. 2.

Kubota, R. et al., "Non-Instrumented Nucleic Acid Amplification (NINA) for Rapid Detection of *Ralstonia solanacearum* Race 3 Biovar 2," Biological Engineering Transactions, 2011, pp. 69-80, vol. 4, No. 2.

Kubota, R. et al., "Real-Time Duplex Applications of Loop-Mediated AMPlification (LAMP) by Assimilating Probes," International Journal of Molecular Sciences, 2015, pp. 4786-4799, vol. 16.

Liu, H.-B. et al., "Development of an isothermal amplification-based assay for the rapid visual detection of *Salmonella* bacteria," Journal of Dairy Science, Jul. 12, 2017, pp. 7016-7025, vol. 100, No. 9.

Liu, M.-L. et al., "Loop-mediated isothermal amplification of *Neisseria gonorrhoeae* porA pseudogene: a rapid and reliablemethod to detect gonorrhea, "AMB Express, 2017, seven pages, vol. 7, No. 48.

Liu, W. et al., "Establishment of an accurate and fast detection method using molecular beacons in loop-mediated isothermalamplification assay," Scientific Reports, 2017, nine pages, vol. 40125.

Meagher, R. J. et al., "Impact of Primer Dimers and Self-Amplifying Hairpins on Reverse Transcription Loop-Mediated Isothermal Amplification Detection of Viral RNA," Analyst, 2018, 32 pages, No. 10.1039/C7AN01897E.

Melendez, J. H. et al., "Antimicrobial Susceptibility of *Neisseria gonorrhoeae* Isolates in Baltimore, Maryland, 2016: The Importance of Sentinel Surveillance in the Era of Multi-Drug-Resistant Gonorrhea," Antibiotics, 2018, seven pages, vol. 7, No. 77.

Melendez, J. H. et al., "Molecular Characterization of Markers Associated With Antimicrobial Resistance in *Neisseria gonorrhoeae* Identified From Residual Clinical Samples," Sexually Transmitted Diseases, May 2018, pp. 312-315, vol. 45, No. 5.

Nadeau, J. G. et al., "Real-Time, Sequence-Specific Detection of Nucleic Acids during Strand Displacement Amplification," Analytical Biochemistiy, 1999, pp. 177-187, vol. 276.

Nazarenko, I. A. et al., "A closed tube format for amplification and detection of DNA based on energy transfer," Nucleic Acids Research, 1997, pp. 2516-2521, vol. 25, No. 12.

Nazarenko, I. et al., "Multiplex quantitative PCR using self-quenched primers labeled with a single fluorophore," Nucleic Acids Research, 2002, seven pages, vol. 30, No. 9 e37.

Nazarenko. I., et al., "Effect of primary and secondary structure of oligodeoxyribonucleotides on the fluorescent properties of conjugated dyes," Nucleic Acids Research, 2002, pp. 2089-2095, vol. 30, No. 9.

Notomi, T. et al., "Loop-mediated isothermal amplification of DNA," Nucleic Acids Research, 2000, seven pages, vol. 28, No. 12 e63.

Panpradist, N. et al., "Swab Sample Transfer for Point-Of-Care Diagnostics: Characterization of Swab Types and ManualAgitation Methods," PLOS ONE, Sep. 2014, 11 pages, vol. 9, No. 9, e105786.

Papp, J. R. et al., "Recommendations for the Laboratory-Based Detection of *Chlamydia trachomatis* and *Neisseria gonorrhoeae*" Centers for Disease Control and Prevention, Recommendations and Reports, Mar. 14, 2014, 21 pages, [Online] [Retrieved on May 19, 2021], Retrieved from the Internet <URL https://www.cdc.gov/mmwr/preview/mmwrhtml/rr6302a1.htm>.

PCT International Search Report and Written Opinion, PCT Application No. PCT/US2021/022192, dated Jul. 9, 2021, 16 pages.

Peterson, S. W. et al., "A Comparison of Real-Time Polymerase Chain Reaction Assays for the Detection of Antimicrobial Resistance Markers and Sequence Typing From Clinical Nucleic Acid Amplification Test Samples and Matched *Neisseria gonorrhoeae* Culture," Sexually Transmitted Diseases, Feb. 2018, pp. 92-95, vol. 45, No. 2.

Priye, A. et al., "A smartphone-based diagnostic platform for rapid detection of Zika, chikungunya, and dengue viruses," Scientific Reports, Mar. 2017, 11 pages, vol. 7, No. 44778.

Tanner, N. A. et al., "Simultaneous multiple target detection in real-time loop-mediated isothermal amplification," BioTechniques, Aug. 2012, pp. 81-89, vol. 53, No. 2.

Tanner, N. A., et al., "Visual detection of isothermal nucleic acid amplification using pH-sensitive dyes," BioTechniques, Feb. 2015, pp. 59-68, vol. 58, No. 2.

Tuite, A. R. et al., "Impact of Rapid Susceptibility Testing and Antibiotic Selection Strategy on the Emergence and Spread of Antibiotic Resistance in Gonorrhea," The Journal of Infectious Diseases, Nov. 1, 2017, pp. 1141-1149, vol. 216, No. 9.

Unemo, M. et al., "The novel 2016 WHO *Neisseria gonorrhoeae* reference strains for global quality assurance of laboratory investigations: phenotypic, genetic and reference genome characterization, "Journal of Antimicrobial Chemotherapy, 2016, pp. 3096-3108, vol. 71.

Whiley, D. M. et al., "Molecular Antimicrobial Resistance Surveillance for *Neisseria gonorrhoeae*, Northern Territory, Australia," Emerging Infectious Diseases, Sep. 2017, pp. 1478-1485, vol. 23, No. 9.

Yaren, O. et al., "Point of sampling detection of Zika virus within a multiplexed kit capable of detecting dengue and chikungunya," BMC Infectious Diseases, 2017, 13 pages.

Yongkiettrakul, S. et al., "Simple detection of single nucleotide polymorphism in *Plasmodium falciparum* by SNP-LAMP assay combined with lateral flow dipstick," Parasitology International, 2017, pp. 964-971, vol. 66.

Zerilli, F. et al., "Methylation-Specific Loop-Mediated Isothermal Amplification for Detecting Hypermethylated DNA in Simplex and Multiplex Formats," Clinical Chemistry, 2010, pp. 1287-1296, vol. 56, No. 8.

Zhang, C. et al., "Establishment and application of a real-time loop-mediated isothermal amplification system for the detection of CYP2C19 polymorphisms," Scientific Reports, Jun. 2016, seven pages, vol. 6, No. 26533.

\* cited by examiner

| Well | Sample Name | Cq Ch1 |
|---|---|---|
| ● A1 | Ct gDNA 10E-01 dilution | 16.18 |
| ● A2 | Ct gDNA 10E-02 dilution | 17.21 |
| ● A3 | Ct gDNA 10E-03 dilution | 20.48 |
| ● A4 | Ct gDNA 10E-04 dilution | 23.90 |
| ● A5 | Ct gDNA 10E-05 dilution | 26.75 |
| ● A6 | Ct gDNA 10E-06 dilution | 30.08 |
| ● A7 | Ct gDNA 10E-07 dilution | 108.83 |
| ● A8 | NTC | 105.88 |
| ○ B1 | Ct gDNA 10E-01 dilution | 15.87 |
| ○ B2 | Ct gDNA 10E-02 dilution | 17.78 |

FIG. 3 (Cont.)

| Well | Sample Name | Cq Ch1 |
| --- | --- | --- |
| ● A1 | 10E-01 gDNA ATCC 5 | 20.85 |
| ● A2 | 10E-02 gDNA ATCC 5 | 22.16 |
| ● A3 | 10E-03 gDNA ATCC 5 | 25.36 |
| ● A4 | 10E-04 gDNA ATCC 5 | 28.35 |
| ● A5 | 10E-05 gDNA ATCC 5 | 31.41 |
| ● A6 | 10E-06 gDNA ATCC 5 | 37.56 |
| ● A7 | 10E-07 gDNA ATCC 5 | 34.64 |
| ● A8 | NTC | |
| ● B1 | 10E-01 gDNA ATCC 5 | 20.30 |
| ● B2 | 10E-02 gDNA ATCC 5 | 21.95 |

FIG. 4 (Cont.)

| Well | Sample Name | Cq Ch1 |
| --- | --- | --- |
| ● A1 | 10E0 (stock) gDNA | 13.71 |
| ● A2 | 10E-1 gDNA RPMI 8 | 14.84 |
| ● A3 | 10E-2 gDNA RPMI 8 | 17.49 |
| ● A4 | 10E-3 gDNA RPMI | 19.50 |
| ● A5 | 10E-4 gDNA RPMI 8 | 23.94 |
| ● A6 | 10E-5 gDNA RPMI 8 | |
| ● A7 | 10E-6 gDNA RPMI 8 | 25.77 |
| ● A8 | 10E-7 gDNA RPMI 8 | |
| ● B1 | 10E0 (stock) gDNA | 12.95 |
| ● B2 | 10E-1 gDNA RPMI 8 | 14.51 |

FIG. 5 (Cont.)

LOOPED PRIMER AND LOOP-DE-LOOP METHOD FOR DETECTING TARGET NUCLEIC ACID

1. CROSS-REFERENCE TO RELATED APPLICATIONS

This application claims priority to U.S. Provisional Patent Application No. 62/989,140 filed on Mar. 13, 2020, which is incorporated by reference in its entirety.

2. SEQUENCE LISTING

The instant application contains a Sequence Listing with 22 sequences, which has been submitted via EFS-Web and is hereby incorporated herein by reference in its entirety. Said ASCII copy, created on Apr. 23, 2021, is named 48397US_CRF_sequencelisting.txt, and is 5,344 bytes in size.

3. BACKGROUND

Methods of detecting a target nucleic acid using complementarity of nucleic acid sequences have been improved or modified variously from traditional Southern hybridization up to the present date. Particularly, the establishment of various in vitro nucleic acid amplification methods, such as polymerase chain reaction (PCR), strand displacement amplification (SDA), nucleic acid sequence-based amplification (NASBA), rolling circle amplification (RCA), and loop-mediated isothermal amplification (LAMP), have enabled smaller amounts of the target nucleic acid to be detected. The methods have been used for sequence-specific detection and quantification of a target nucleic acid in a sample for medical diagnose of infection, determination of mutant genotypes, detection of single nucleotide polymorphisms (SNPs) and point mutations, etc. Nucleic acid amplification methods have been the gold standard for testing because of their high specificity and sensitivity.

However, current nucleic acid amplification methods have limitations because amplification reaction and signal detection require controlled environment and precise measurement with expensive instruments. Thus, the methods are often cost-prohibitive for use in point-of-care situations. Additionally, the methods are not optimized for detection of multiplexed targets in single patient samples. Detection of multiplexed targets may be accomplished by signal multiplexing in single-pot reactions (fluorescent spectral multiplexing, arrays of electrochemical detectors), physical separation of multiple reactions into unique reaction vessels, or a combination thereof. However, in the case of a CLIA waived test, no more than three simple steps must be required by the user to simultaneously query a panel of nucleic acid targets using a single patient sample. Accordingly, physical separation of samples into discrete chambers quickly becomes infeasible for CLIA waived tests, unless a complicated device or disposable automatically handles processing. Spectral multiplexing with fluorescence can reduce the number of unique reactions required to target a panel of nucleic acid targets, but spectral multiplexing LAMP reactions has required dramatic sacrifices in assay speed or signal strength, dampening prospects for successful application to POC testing.

Therefore, there is a need for development of a new method that enables easy amplification and detection of target nucleic acid, particularly multiplexed targets, with high sensitivity and specificity at a low cost.

4. SUMMARY

The present disclosure provides a new amplification method that enables easy detection of a target nucleic acid in a closed system. The method allows detection of a small amount of a target nucleic acid with high specificity and sensitivity by using a looped primer having a biosensor pair. The biosensor pair allows determination of loop-de-loop ("LDL") amplification of a target sequence by detecting conformational change of the looped primer, for example, by using fluor/quencher FRET techniques. Additionally, use of multiple biosensors enables detection of multiplexed targets in a single tube. The looped primer can be used combined not only with loop-mediated isothermal amplification (LAMP) but with any other nucleic acid amplification method utilizing a strand displacing polymerase.

Applicant has demonstrated that the loop-de-loop amplification method allows sequence-specific amplification of a target nucleic acid molecule with improved sensitivity and specificity at a faster turnaround time compared to previously known methods involving inhibitory fluorescent probes, such as DARQ (detection of amplification by releasing of quenching), and OSD (one-step displacement) probes. Further, the loop-de-loop amplification method allows real-time detection of amplification signals unlike QUASR (quenching of unincorporated amplification signal reporters). Since the loop-de-loop method provides a strong signal even with crude samples, the method can be performed by a low-cost instrument.

Accordingly, the present invention provides a method for detecting one or more target nucleic acids present in a sample using a looped primer (e.g., a fluorophore-labeled primer). The fluorophore-labeled primer is a fluorophore-labeled oligonucleotide having complementarity to a target nucleic acid and a contiguous loop sequence that is labeled internally at or near the 5' terminus of the unmodified primer sequence with a biosensor pair, e.g., a fluorophore or quencher molecule. The fluorophore-labeled primer is labeled at or near the 5' terminus of the added loop sequence with a quencher or fluorophore, respectively, to enable FRET with the internal label described in the previous point. In some embodiments, the fluorophore-labeled primer is labeled at or near the 5' terminus of the added loop sequence with a fluorophore and an internal site with a quencher. The fluorophore-labeled primer further contains a first clamping sequence at the loop sequence's 3' end (at the intersection with the unmodified primer sequence). This sequence can overlap the unmodified primer sequence, be directly adjacent to the unmodified primer sequence, or be spaced apart from the unmodified primer sequence. The sequence can comprise dNTPs, locked nucleic acids, or any other form of nucleic acid modification or substitution.

The melting temperature of said clamping sequence is preferably about 10° C. higher than the extension temperature of the assay using a strand displacing polymerase, but can be lower than, equal to, or any amount higher than the extension temperature of the assay.

In the case where the clamping sequence's melting temperature is lower than the reaction's extension temperature, real time detection can be replaced in this method by end-point detection (cooling the reaction to near or below the Tm of the clamping sequence). In this case, there is no inhibition of the reaction, even when using the looped primers at full strength (100% substitution of unmodified primer with a looped primer analogue).

In the case where the clamping sequence's melting temperature is equal to the reaction's extension temperature, real time detection is still viable, but there can be higher background fluorescence until cooling the reaction for an endpoint determination.

In the case where the clamping sequence's melting temperature is greater than the reaction's extension temperature, real time detection is the dominant mode of operation, and there will be minimal background fluorescence.

The fluorophore-labeled primer further contains a spacing sequence that separates the internally conjugated fluorophore or quencher an appropriate distance from the 5'-end quencher or fluorophore to inhibit FRET when the primer is in a linear (extended) conformation, and therefore increases fluorescence. The spacing sequence is arbitrary in sequence and length, and can include deoxyribonucleotides, locked nucleic acids, etc. The length can be 25 nucleotides, but can be shorter or longer.

The fluorophore-labeled primer further contains a second clamping sequence at or near the loop sequence's 5' end, that is the reverse complement of the first clamping sequence. The fluorophore-labeled primer can further include additional DNA barcodes, probes, or sequences further to the 5' end of the loop-de-loop oligonucleotide. The sequence can comprise dNTPs, locked nucleic acids, or any other form of nucleic acid modification or substitution.

The melting temperature of the second clamping sequence, paired with the first clamping sequence is preferably 10° C. higher than the extension temperature of the assay using a strand displacing polymerase, but can be lower than, equal to, or any amount higher than the extension temperature of the assay.

The looped, fluorophore-labeled primer can further comprise an additional sequence, molecule, purification tag, bead, or other moiety at the 5' end to enable further applications, such as: nucleic acid capture, molecular barcoding, magnetic separations, column purifications, electrophoretic separation. Probe capture oligonucleotides patterned onto a substrate can be used to capture amplified products, thus creating a fluorescent, colorimetric, luminescent, or other band or zone.

The looped primers can be titrated into the assay to varying degrees to minimize cost or increase sensitivity and specificity.

The looped primers as described herein can be designed with a sensor molecule other than a fluorophore, for example, a reporter molecule that provides luminesce, change of color, or other measurable signal in close proximity or when moved sufficiently apart. In some cases, a biosensor, such as NanoLuc, Nanobit, NonoBRET, can be used.

In the case where luminescent proteins are used, reduction in signal can be the key indicator of positive reactions. In some embodiments, endpoint analysis by bioluminescence can be done.

An enzyme capable of strand displacement can be used for amplification of a target sequence. Other reagents as required by the chosen nucleic acid amplification method can be further used.

The method provided herein can reduce false positive and nonspecific amplification detection, because it allows specific detection of fluorescent signals in high background conditions with high concentrations of nontarget RNA or DNA. The fluorescence detection allows specific detection of only those amplicons and products that incorporate the labeled primer(s). This allows specific detection even when crude or unprocessed samples are used, such as genital swabs, feces, saliva, urine, blood, plant material, soil, environmental samples, etc.

In some embodiments, the method can be applied for detection of more than one unique nucleic acid targets. In such duplexed, triplexed, or higher-order multiplexed LAMP assays, targets may be differentially labeled. For example, one target is labeled with FAM and the other is labeled with Cy5. In some cases, the detection is spectrally multiplexed to detect a single nucleic acid target with multiple labeled primers, to further reduce the ability to distinguish true from false positives. In some cases, the detection uses a single label, such as FAM, for multiple targets, and each target's identity can be determined based on analysis of the real-time or endpoint signal depending upon the specific context of the assay (e.g., relative signal strength, time to result, etc.). In some cases, multiplexing may be accomplished by carrying out reactions in physically reaction chambers. In some cases, multiplexing may be accomplished in a single reaction chamber.

The method provided herein minimizes inhibition compared to other real time LAMP displacement probe technologies, making this method highly sensitive. Titration into assays demonstrates full reaction speed is maintained for at least 50% of the Loop primer substitution. Titration into assays demonstrates full reaction speed is maintained for at least 25% of the inner primer substitution.

The looped primer provided herein can be used for loop mediated amplification (LAMP), that utilizes a strand displacing polymerase, such as a polymerase isolated or adapted from *Geobacillus stearothermophilus* (previously *Bacillus stearothermophilus*). In this case, the looped primer can be used together with other primers for LAMP, including the forward inner primer, backwards inner primer, loop forward primer, loop backward primer, F3 primer, and B3 primer.

In some embodiments, primers and possibly other reaction components are dried using a process, including but not limited to the process of lyophilization. The dried primers can be included in a diagnostic kit. In preferred embodiments, the process of lyophilization does not impact sensitivity of the LAMP primer set.

In one aspect, the present disclosure provides a looped primer for loop-de-loop amplification (LdL) of a target sequence, comprising from 5' to 3': a first sensor molecule; a first clamping oligonucleotide; a spacing oligonucleotide; a second clamping oligonucleotide, wherein the first clamping oligonucleotide, the spacing oligonucleotide and the second clamping oligonucleotide can form a hairpin structure at a temperature below the melting temperature (Tm) of the first and second clamping oligonucleotides; a second sensor molecule, wherein the first sensor molecule and the second sensor molecule are a first biosensor pair; and a first primer sequence complementary to a first binding site on the target sequence.

In some embodiments, the second clamping oligonucleotide is complementary to the first clamping oligonucleotide.

In some embodiments, the first biosensor pair is an energy donor and acceptor pair. In some embodiments, the first biosensor pair is an energy donor and acceptor pair for fluorescence resonance energy transfer (FRET) or bioluminescence resonance energy transfer (BRET). In some embodiments, the first sensor molecule is a FRET fluorophore and the second sensor molecule is a FRET quencher. In some embodiments, the first sensor molecule is a FRET quencher and the second sensor molecule is a FRET fluorophore. In some embodiments, the first sensor molecule is a BRET energy donor and the second sensory molecule is a BRET energy acceptor. In some embodiments, the first sensor molecule is a BRET energy acceptor and the second sensory molecule is a BRET energy donor. In some embodiments, the first sensor molecule and the second sensor molecule can form a complex that generates a detectable light signal.

In some embodiments, the melting temperature (Tm) of the first and second clamping oligonucleotides is above 60° C. In some embodiments, the melting temperature (Tm) of the first and second clamping oligonucleotides is above 65° C. In some embodiments, the melting temperature (Tm) of the first and second clamping oligonucleotides is above 70° C. In some embodiments, the melting temperature (Tm) of the first and second clamping oligonucleotides is above 80° C. In some embodiments, the melting temperature (Tm) of the first and second clamping oligonucleotides is from 70 to 80° C. In some embodiments, the melting temperature (Tm) of the first and second clamping oligonucleotides is from 72.5 to 77.5° C. In some embodiments, the melting temperature (Tm) of the first and second clamping oligonucleotides is about 75° C. In some embodiments, the melting temperature (Tm) of the first and second clamping oligonucleotides is below 60° C. In some embodiments, the melting temperature (Tm) of the first and second clamping oligonucleotides is from 60 to 65° C.

In some embodiments, the first clamping oligonucleotide and the second clamping oligonucleotide are from 3 to 10-nucleotide long. In some embodiments, the first clamping oligonucleotide and the second clamping oligonucleotide are from 3 to 7-nucleotide long. In some embodiments, the first clamping oligonucleotide and the second clamping oligonucleotide are 6-nucleotide long. In some embodiments, the spacing oligonucleotide is from 5 to 35-nucleotide long. In some embodiments, the spacing oligonucleotide is from 10 to 20-nucleotide long. In some embodiments, the spacing oligonucleotide is from 13 to 18-nucleotide long. In some embodiments, the spacing oligonucleotide is 13-nucleotide long. In some embodiments, the first clamping oligonucleotide, the spacing oligonucleotide, and the second clamping oligonucleotide together are from 15 to 35-nucleotide long. In some embodiments, the first clamping oligonucleotide, the spacing oligonucleotide, and the second clamping oligonucleotide together are from 20 to 30-nucleotide long. In some embodiments, the spacing oligonucleotide, and the second clamping oligonucleotide together are from 23 to 28-nucleotide long.

In some embodiments, the first clamping oligonucleotide, the spacing oligonucleotide, and the second clamping oligonucleotide comprise (i) a nucleobase selected from adenine, guanine, cytosine, thymine, and uracil, (ii) a locked nucleic acid, (iii) a 2" O-methyl RNA base, (iv) a phosphorothioated DNA base, (v) a phosphorothioated RNA base, (vi) a phosphorothioated 2"-O-methyl RNA base, or (vii) a combination thereof.

In some embodiments, the looped primer further comprises a first additional oligonucleotide at 5' end of the looped primer. In some embodiments, the looped primer further comprises a second additional oligonucleotide between the first sensor molecule and the first clamping oligonucleotide.

In some embodiments, the first or the second additional oligonucleotide is a barcode sequence.

In some embodiments, the target sequence is specific to a pathogen genome. In some embodiments, the target sequence is specific to *Chlamydia trachomatis*. In some embodiments, the target sequence is from orf8 or cds2. In some embodiments, the looped primer comprises the oligonucleotide of SEQ ID NO: 15.

In some embodiments, the target sequence is specific to *Neisseria gonorrhoeae*. In some embodiments, the target sequence is from porA or glnA. In some embodiments, the looped primer comprises the oligonucleotide of SEQ ID NO: 5 or 7.

In some embodiments, the target sequence is specific to virus. In some embodiments, the virus is SARS-CoV-2.

In some embodiments, the target sequence is specific to *Homo sapiens*. In some embodiments, the target sequence is from tbc1d3. In some embodiments, the looped primer comprises the oligonucleotide of SEQ ID NO: 22.

In another aspect, the present disclosure provides a primer mixture for loop-de-loop amplification of a target sequence, comprising the looped primer provided herein.

In some embodiments, the primer mixture further comprises (i) a forward inner primer (FIP), (ii) a backward inner primer (BIP), (iii) a forward primer (F3), and a backward primer (B3), wherein the FIP, the BIP, the F3, and the B3 bind to six different binding sites on the target sequence. In some embodiments, the primer mixture comprises (i) a loop forward primer (LF) and (ii) a loop backward primer (LB), wherein the LF and the LB bind to two different binding sites on the target sequence. In some embodiments, the FIP, the BIP, the F3, the B3, the LF, or the LB binds to the first binding site on the target sequence. In some embodiments, the FIP binds to the first binding site, and the ratio between the amounts of the FIP and the looped primer in the primer mixture is 1:1, 2:1, 3:1, 4:1, 5:1, 6:1, 7:1, 8:1, or 9:1. In some embodiments, the BIP binds to the first binding site, and the ratio between the amounts of the BIP and the looped primer in the primer mixture is 1:1, 2:1, 3:1, 4:1, 5:1, 6:1, 7:1, 8:1, or 9:1. In some embodiments, the LF binds to the first binding site, and the ratio between the amounts of the LF and the looped primer in the primer mixture is 1:1, 2:1, 3:1, 4:1, 5:1, 6:1, 7:1, 8:1, or 9:1. 52. In some embodiments, the LB binds to the first binding site, and the ratio between the amounts of the LB and the looped primer in the primer mixture is 1:1, 2:1, 3:1, 4:1, 5:1, 6:1, 7:1, 8:1, or 9:1.

In some embodiments, the F3 comprises the oligonucleotide of SEQ ID NO: 1, the B3 comprises the oligonucleotide of SEQ ID NO: 2, the FIP comprises the oligonucleotide of SEQ ID NO: 3, the BIP comprises the oligonucleotide of SEQ ID NO: 4, the LF comprises the oligonucleotide of SEQ ID NO: 6, or the LB comprises the oligonucleotide of SEQ ID NO: 8.

In some embodiments, the F3 comprises the oligonucleotide of SEQ ID NO: 1, the B3 comprises the oligonucleotide of SEQ ID NO: 2, the FIP comprises the oligonucleotide of SEQ ID NO: 3, the BIP comprises the oligonucleotide of SEQ ID NO: 4, the LF comprises the oligonucleotide of SEQ ID NO: 6, and the LB comprises the oligonucleotide of SEQ ID NO: 8.

In some embodiments, the F3 comprises the oligonucleotide of SEQ ID NO: 9, the B3 comprises the oligonucleotide of SEQ ID NO: 10, the FIP comprises the oligonucleotide of SEQ ID NO: 11, the BIP comprises the oligonucleotide of SEQ ID NO: 12, the LF comprises the oligonucleotide of SEQ ID NO: 13, or the LB comprises the oligonucleotide of SEQ ID NO: 14.

In some embodiments, the F3 comprises the oligonucleotide of SEQ ID NO: 9, the B3 comprises the oligonucleotide of SEQ ID NO: 10, the FIP comprises the oligonucleotide of SEQ ID NO: 11, the BIP comprises the oligonucleotide of SEQ ID NO: 12, the LF comprises the oligonucleotide of SEQ ID NO: 13, and the LB comprises the oligonucleotide of SEQ ID NO: 14.

In some embodiments, the F3 comprises the oligonucleotide of SEQ ID NO: 16, the B3 comprises the oligonucleotide of SEQ ID NO: 17, the FIP comprises the oligonucleotide of SEQ ID NO: 18, the BIP comprises the oligonucleotide of SEQ ID NO: 19, the LF comprises the oligonucleotide of SEQ ID NO: 20, or the LB comprises the oligonucleotide of SEQ ID NO: 21.

In some embodiments, the F3 comprises the oligonucleotide of SEQ ID NO: 16, the B3 comprises the oligonucleotide of SEQ ID NO: 17, the FIP comprises the oligonucleotide of SEQ ID NO: 18, the BIP comprises the oligonucleotide of SEQ ID NO: 19, the LF comprises the oligonucleotide of SEQ ID NO: 20, and the LB comprises the oligonucleotide of SEQ ID NO: 21.

In some embodiments, the primer mixture further comprises a second looped primer, wherein the second looped primer comprises: a third sensor molecule; a third clamping oligonucleotide; a second spacing oligonucleotide; a fourth clamping oligonucleotide, wherein the third clamping oligonucleotide, the second spacing oligonucleotide and the fourth clamping oligonucleotide can form a hairpin structure at a temperature below the melting temperature (Tm) of the third and fourth clamping oligonucleotides; a fourth sensor molecule, wherein the third sensor molecule and the fourth sensor molecule are a second biosensor pair, and the second biosensor pair differs from the first biosensor pair; and a second primer sequence complementary to a first binding site on a second target sequence.

In some embodiments, the third clamping oligonucleotide is complementary to the fourth clamping oligonucleotide. In some embodiments, the target sequence and the second target sequence are identical. In some embodiments, the target sequence and the second target sequence are different.

In some embodiments, the primer mixture further comprises (i) a second forward inner primer (SFIP), (ii) a second backward inner primer (SBIP), (iii) a second forward primer (SF3), and (iv) a second backward primer (SB3), wherein the SFIP, the SBIP, the SF3, and the SB3 bind to six different binding sites on the second target sequence.

In some embodiments, the primer mixture further comprises (i) a second loop forward primer (SLF) and (ii) a second loop backward primer (SLB), wherein the SLF and the SLB bind to two different binding sites on the second target sequence. In some embodiments, the primer mixture further comprises a third looped primer, wherein the third looped primer comprises: a fifth sensor molecule; a fifth clamping oligonucleotide; a third spacing oligonucleotide; a sixth clamping oligonucleotide, wherein the fifth clamping oligonucleotide, the third spacing oligonucleotide and the sixth clamping oligonucleotide can form a hairpin structure at a temperature below the melting temperature (Tm) of the fifth and sixth clamping oligonucleotides; a sixth sensor molecule, wherein the fifth sensor molecule and the sixth sensor molecule are a third biosensor pair, and the third biosensor pair differs from the first biosensor pair and the second biosensor pair; and a second primer sequence complementary to a first binding site on a third target sequence. In some embodiments, the fifth clamping oligonucleotide is complementary to the sixth clamping oligonucleotide. In some embodiments, the target sequence, the second target sequence and the third target sequence are identical. In some embodiments, the target sequence, the second target sequence and the third target sequence are different. In some embodiments, the primer mixture further comprises (i) a third forward inner primer (TFIP), (ii) a third backward inner primer (TBIP), (iii) a third forward primer (TF3), and (iv) a third backward primer (TB3), wherein the TFIP, the TBIP, the TF3, and the TB3 bind to six different binding sites on the third target sequence. In some embodiments, the primer mixture further comprises (i) a third loop forward primer (TLF) and (ii) a third loop backward primer (TLB), wherein the TLF and the TLB bind to two different binding sites on the third target sequence. In some embodiments, the primer mixture further comprises a fourth looped primer. In some embodiments, the primer mixture further comprises a fifth looped primer.

In yet another aspect, the present disclosure provides a dried primer mixture obtained by lyophilizing the looped primer or the primer mixture provided herein.

In one aspect, the present disclosure provides a kit for loop-de-loop amplification of a target sequence, comprising the looped primer, the primer mixture, or the dried primer mixture provided herein. In some embodiments, the kit further comprises polymerase, wherein the polymerase is optionally a *Bacillus stearothermophilus* polymerase. In some embodiments, the kit further comprises dNTPs, $MgSO_4$, and a buffer. In some embodiments, the kit further comprises a reverse transcriptase. In some embodiments, the kit further comprises an RNase inhibitor. In some embodiments, the RNase inhibitor is a porcine or murine RNase inhibitor.

In another aspect, the present disclosure provides a method of detecting the target sequence in a sample, comprising the steps of: providing a sample; adding (i) the primer, (ii) the primer mixture, or (iii) a reconstituted primer mixture obtained by rehydrating the dried primer mixture as described herein, and a polymerase to the sample, thereby generating a reaction mixture; and incubating the reaction mixture at 50-85° C. In some embodiments, the incubation is performed at 50-70° C. In some embodiments, the incubation is performed at 60-65° C. In some embodiments, the incubation is performed at 62-65° C. In some embodiments, the polymerase is a *Bacillus stearothermophilus* polymerase. In some embodiments, the method further comprises the step of detecting a signal from the reaction mixture. In some embodiments, the signal is fluorescence signal. In some embodiments, the step of detecting is performed during the step of incubation. In some embodiments, the method further comprises the step of determining the presence or the absence of the target sequence in the sample.

In some embodiments, the method further comprises the preceding step of preparing the sample. In some embodiments, the step of preparing the sample comprises interacting RNA molecules with a reverse transcriptase, thereby generating the sample comprising DNA molecules. In some embodiments, the step of preparing the sample further comprises preheating the RNA molecules before or during interaction with the reverse transcriptase. In some embodiments, the reaction mixture further comprises an RNase inhibitor. In some embodiments, the RNase inhibitor is a porcine or murine RNA inhibitor.

In some embodiments, the sample comprises purified RNA, purified DNA, whole SARS-CoV-2 virus, whole human cells, saliva or nasal swab, or nasal or nasopharyngeal swab. In some embodiments, the sample comprises genomic DNA, synthetic DNA, whole bacteria or whole human cells from vaginal swab.

5. BRIEF DESCRIPTION OF THE DRAWINGS

FIG. 1 illustrates the structure of a looped primer and how DNA amplification proceeds in the loop-de-loop method.

FIG. 2A provides results from LAMP assays for *Chlamydia trachomatis* (CT) and *Neisseria gonorrhoeae* (NG), visualized with an intercalating dye (SYTO). Amplification is rapid (<30 min) over at least 5 logs of [DNA] for CT and 6 logs for NG. NG assay analytical sensitivity (LOD50) is 35 cp/10 µL reaction by PROBIT analysis.

FIG. 2B provides a readout from target amplification using the novel looped primer. The results show extremely bright real-time detection of the target with minimal inhibition and enhanced specificity over SYTO dye.

FIG. 2C provides detection of *Neisseria gonorrhoeae* with novel looped primer. The results show that the method is repeatable and generates rapid, robust, high signal-to-noise ratio amplification. Probes eliminate false positives.

FIG. 3 is a plot of real-time fluorescence signals over time indicating amplification of target nucleic acid of *Chlamydia trachomatis* using Loop-de-Loop method with FAM-labeled LF primer at 50% substitution. Both positive and negative samples were tested as indicated on the right table. Each "cycle" on the y-axis represents 30 seconds of elapsed time at 65 degrees Celsius.

FIG. 4 is a plot of real-time fluorescence signals over time indicating amplification of target nucleic acid of *Neisseria gonorrhoeae* using Loop-de-Loop method with FAM-labeled LF primer at 50% substitution. Both positive and negative samples were tested as indicated on the right table. Each "cycle" on the y-axis represents 30 seconds of elapsed time at 65 degrees Celsius.

FIG. 5 is a plot of real-time fluorescence signals over time indicating amplification of target nucleic acid of *Homo sapiens* using Loop-de-Loop method with FAM-labeled LF primer at 50% substitution. Both positive and negative samples were tested as indicated on the right table. Each "cycle" on the y-axis represents 30 seconds of elapsed time at 65 degrees Celsius.

FIG. 6 provides images of tubes containing 4 positive (left) and 4 negative (right) reactions with Loop-de-Loop primers. Fluorescence was excited with a blue LED, shone through a blue gel filter, and emission was visualized with an amber plastic filter held up to a camera phone.

FIG. 7 provides images of tubes containing dried (lyophilized) mixtures for Looped Primer assays for *Chlamydia trachomatis* (top), *Neisseria gonorrhoeae* (center), and *Homo sapiens* (bottom) prepared by lyophilization in PCR tubes.

FIG. 8 provides real-time fluorescence signals indicating amplification of target nucleic acid of *Chlamydia trachomatis, Neisseria gonorrhoeae*, and *Homo sapiens* in the Loop-de-Loop reaction using the dried mixtures of FIG. 7 which were reconstituted before use. The results show maintained assay activity and sensitivity of the dried and then reconstituted primers.

FIGS. 9A (first test) and 9B (second test) plot times required to obtain results from Loop-de-loop LAMP reaction using the POP7b (*H. sapiens* RNA transcript) or ORF1ab (SARS-CoV-2 genomic RNA) primer set at various temperatures.

FIG. 10 provides a melting curve of loop-de-loop primers targeting a DNA from H. *Sapiens*, C. *Trachomatis*, N. *Gonorrhoeae*, or SARS-CoV-2. The loop-de-loop primers are designed to unfold about 10° C. above the reaction temperature, 65° C. The curve demonstrates that the loop-de-loop primers' stem-loop sequence is responsible for the fluorescent signal.

FIG. 11 provides real-time fluorescent signals from loop-de-loop reactions using primers at 25%, 50%, or 100% strength. In this context, "strength" is the degree to which a primer is substituted with a looped version for the Loop-de-Loop method. The data shows that stronger primers tend to provide bigger signals in exchange of a 1-2 minutes of slowdown in time to result. Loop-de-loop primers at 100% strength slowed assays, but not nearly to the extent of other real-time LAMP displacement probe methods. Each "cycle" on the y-axis represents 30 seconds of elapsed time at 65 degrees Celsius.

FIG. 12 provides relative fluorescent signals from loop-de-loop reactions including both 0.4 µM loop-de-loop primer and 2 µM SYTO intercalating dye. The 2-channel fluorescence data demonstrate identical timing for development of intercalating dye (SYTO) and loop-de-loop signals. There was no signal delay with loop-de-loop versus intercalating dyes, and loop-de-loop reaction provided a bigger signal than SYTO.

FIGS. 13A and 13B show real-time fluorescent signals from amplification of a target sequence of *Chlamydia trachomatis* using loop-de-loop reaction. FIG. 13A is a result from a freshly mixed reaction mixture, and FIG. 13B is a result from a freeze-dried reaction mixture. Freeze-dried assay mixtures were stable for more than 3 months and provided good readouts. The assays were run with 14 replicates, each of Ct E BOUR (a strain of *Chlamydia trachomatis*) at the $LoD_{95}$ (Low positive) of the assay (20.7 copies/µL), plus 2 no template controls (NTCs). There was no change in sensitivity (12/14 each at $LoD_{95}$) or in average time to result (16 min, T-test, P-value=0.66) between the fresh and freeze-dried reaction mixtures.

FIGS. 14A, 14B and 14C show spectrally duplexed fluorescent signals from loop-de-loop amplification of SARS-CoV-2 and human target sequences in single tube reactions (single pot). Dashed-line signals are from SARS-CoV-2 (FAM) and solid-line signals are from human internal control (Cy5). Three types of samples were used—a control sample without target sequences (FIG. 14A), crude human nasal swab (FIG. 14B) and crude human nasal swab combined with heat-inactivated SARS-CoV-2 (intact virus with genomic RNA target sequence) (FIG. 14C). The data show specific amplification signals only in the presence of target sequences. The data further demonstrate spectral multiplexing of reactions with the loop-de-loop method in a single reaction vessel.

FIG. 15A shows real-time fluorescent signals from loop-de-loop amplifications at various concentrations of POP7b primers. Signal strength decreased as the concentration of POP7b primers was reduced (arrow). In multiplexing applications with more than one primer set in a single reaction volume, the concentration of any given primer set will be reduced compared to a reaction in which 100% of the primers belong to a single set. FIG. 15B plots time to result (min) at various concentrations of POP7b primers. Time to result was affected when the primer concentration fell below 40%, which is tolerable for many applications where the advantages of multiplexing more than 2 targets in a single tube outweigh a clinical or market-based need for speed. In the reaction, $10^{-4}$ gBlock DNA was used in 21p L reaction volume.

FIG. 16 shows real-time fluorescent signals from loop-de-loop RT-LAMP amplifications of either an RNA target sequence specific to SARS-CoV-2 (ORF1ab), an RNA target sequence specific to *Homo sapiens* (POP7b), both targets, or neither target, in an unprocessed nasal swab obtained from a coronavirus-positive subject. The nasal swab was eluted directly into loop-de-loop RT-LAMP reagents and diluted to 4 concentrations into reaction mixture. 1× Swab represents the standard concentration of a sample used in this test configuration, in units of swabs eluted per unit volume. In this instance, the SARS-CoV-2 and human RNA primer sets were duplexed in a single tube. Each primer set contained 1 looped primer, each labeled with the same fluorophore and quencher pair (single fluorescence channel). The result was that reactions in which both SARS-CoV-2 and human RNA were detected featured a double-amplification signal. Dilutions that resulted in the detection of both targets are labeled "dual positive"; those resulting in the detection of either target, "single positive"; those resulting in the detection of neither target, "dual negative". This data demonstrated that, for this coronavirus-positive volunteer's swab sample, the real-time Loop-de-Loop RT-LAMP assay was at least 370 times more sensitive than necessary to detect both targets in the reaction.

FIG. 17 shows real-time fluorescent signals from loop-de-loop amplifications of a target sequence specific to SARS-CoV-2 in a nasal swab obtained from a negative subject.

FIG. 18 shows fluorescent signals from multiplexed loop-de-loop amplification of SARS-CoV-2 and human target sequences and demonstrates specificity of the loop-de-loop reactions. Both SARS-CoV-2 and human primer sets were modified for loop-de-loop using FAM-labeled primers, so the dual positive control shows 2 amplification events. The RPPOS is a respiratory pathogen panel positive (Exact Diagnostics LLC) containing genetic material from 22 non-target respiratory pathogens. PRNEG is a background matrix control for the RPPOS product without nucleic acids. The data show that loop-de-loop RT-LAMP reactions to detect SARS-CoV-2 and human targets do not amplify off-target nucleic acids.

Figure 1:
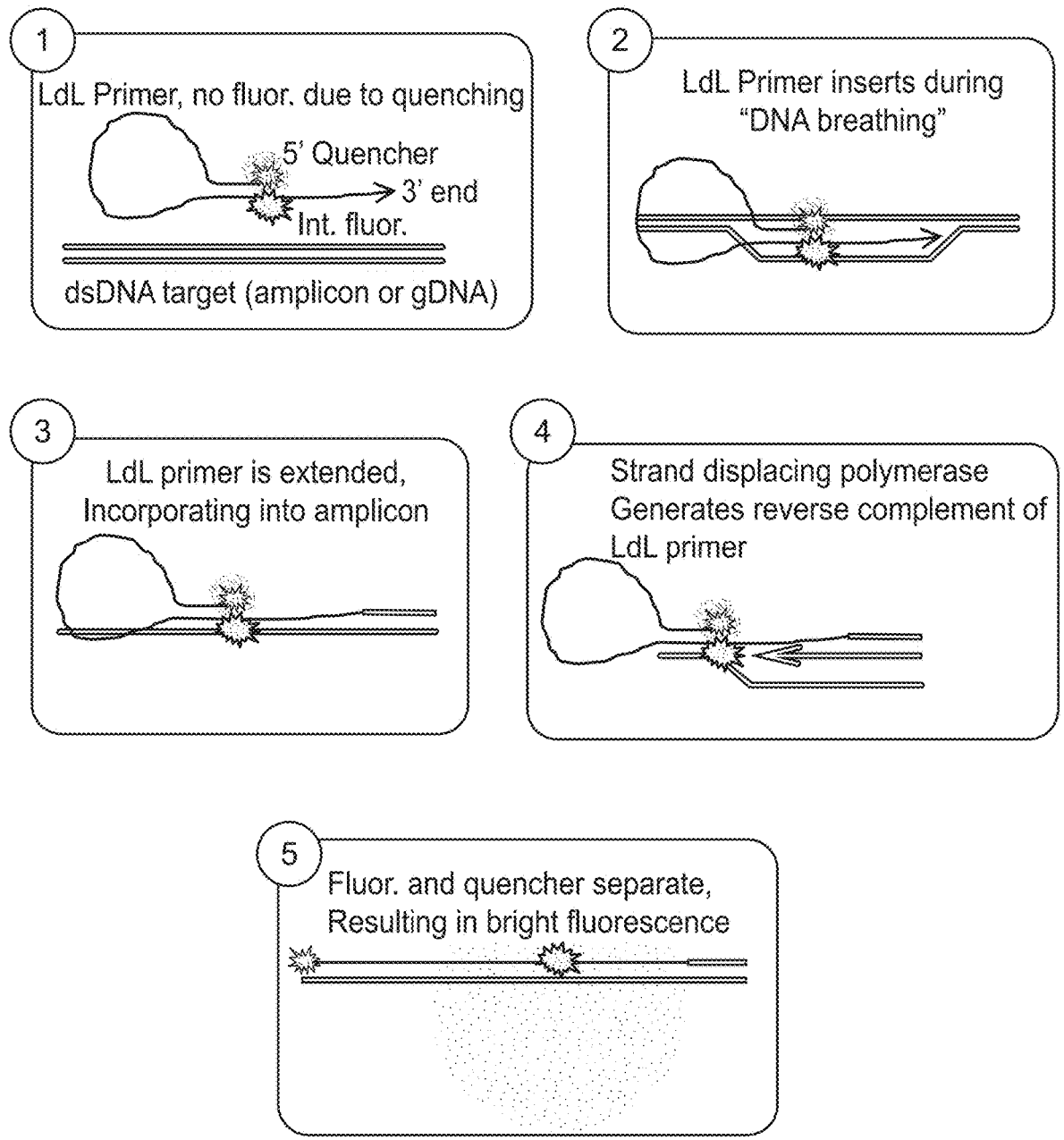

The figures depict various embodiments of the present invention for purposes of illustration only. One skilled in the art will readily recognize from the following discussion that alternative embodiments of the structures and methods illustrated herein may be employed without departing from the principles of the invention described herein.

6. DETAILED DESCRIPTION

6.1. Definitions

Unless defined otherwise, all technical and scientific terms used herein have the meaning commonly understood by a person skilled in the art to which this invention belongs. As used herein, the following terms have the meanings ascribed to them below.

The term "biosensor pair" as used herein refers to a pair of sensor molecules that can generate a detectable signal upon certain physical interactions between the two sensor molecules. For example, the biosensor pair can be a pair of a donor molecule and an acceptor molecule used for Forster resonance energy transfer, such as fluorescence resonance energy transfer (FRET). In this case, fluorescence signals can be generated by distance-dependent transfer of energy from the donor molecule to the acceptor molecule. In other embodiments, the biosensor pair is a pair of sensor molecules used for bioluminescence resonance energy transfer (BRET). In this case, bioluminescence signals can be generated by distance-dependent transfer of energy from the donor molecule to the acceptor molecule. Other biosensor pair known in the art can be used in various embodiments of the present disclosure.

The term "loop-de-loop amplification" or "LdL amplification" as used herein refers to an amplification of a target nucleic acid using a looped primer that can generate a fluorescence signal by distance-dependent transfer of energy.

The term "LOD" as used herein refers to limit of detection. For example, LOD95 is limit of detection, $95^{th}$ percentile. This is the concentration of a target at which the assay is statistically expected to detect a positive result 95% of the time.

6.2. Other Interpretational Conventions

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless otherwise indicated, reference to a compound that has one or more stereocenters intends each stereoisomer, and all combinations of stereoisomers, thereof.

6.3. Looped Primers

In one aspect, the present invention provides a looped primer for loop-de-loop amplification. The looped primer comprises from 5' to 3':

a first sensor molecule;
a first clamping oligonucleotide;
a spacing oligonucleotide;
a second clamping oligonucleotide,
    wherein the first clamping oligonucleotide, the spacing oligonucleotide and the second clamping oligonucleotide can form a hairpin structure at a temperature below the melting temperature ($T_m$) of the first and second clamping oligonucleotides;
a second sensor molecule,
    wherein the first sensor molecule and the second sensor molecule are a first biosensor pair; and
a first primer sequence complementary to a first binding site on the target sequence In some embodiments, the second clamping oligonucleotide is complementary to the first clamping oligonucleotide. In some embodiments, the second clamping oligonucleotide can bind to the first clamping oligonucleotide but is not completely complementary to the first clamping oligonucleotide.

Various biosensors known in the art can be used for the method provided herein. For example, a pair of molecules that change color or produce a measurable signal in a close proximity or in a sufficient distance (e.g. NanoLuc, Nanobit, NonoBRET technologies based on luminescent proteins) can be used.

In some embodiments, the first biosensor pair is an energy donor and acceptor pair. In some embodiments, the first biosensor pair is an energy donor and acceptor pair for Forster resonance energy transfer. In some embodiments, the first biosensor pair is an energy donor and acceptor pair for fluorescence resonance energy transfer (FRET) or bioluminescence resonance energy transfer (BRET). In some embodiments, the first sensor molecule is a FRET fluorophore and the second sensor molecule is a FRET quencher. In some embodiments, the first sensor molecule is a FRET quencher and the second sensor molecule is a FRET fluorophore. In some embodiments, the first sensor molecule is a BRET energy donor and the second sensory molecule is a BRET energy acceptor. In some embodiments, the first sensor molecule is a BRET energy acceptor and the second sensory molecule is a BRET energy donor.

In some embodiments, the FRET quencher is 5IABkFQ, available from Integrated DNA technologies with the tradename, the 5' Iowa Black® FQ. The 5' Iowa Black® FQ is a FRET quencher having broad absorbance spectra ranging from 420 to 620 nm with peak absorbance at 531 nm. This quencher can be used with fluorescein and other fluorescent dyes that emit in the green to pink spectral range. In some embodiments, the quencher is any of the Black Hole Quenchers® (available from Biosearch Technologies), either of the Iowa Black® quenchers (available from Integrated DNA technologies), Zen® quencher (available from Integrated DNA Technologies), any of the Onyx® quenchers (available from Millipore-Sigma), or any of the ATTO® quenchers (available from ATTO-TEC GmbH).

In some embodiments, the FRET fluorophore is i6-FAMK (FAM (fluorescein) azide) available from Integrated DNA technologies with the name, Int 6-FAM (Azide). This form of FAM can be attached to the oligonucleotide using click chemistry. The internal version of this modification is attached to the oligo through a dT base. A dT nucleotide can be added at the position of the modification. Alternatively, to avoid adding an extra nucleotide, an existing T nucleotide in the sequence can be replaced with the required modification. In some embodiments, the fluorophore is Cy3, Cy5, TAMRA, or Yakima Yellow® (available from Integrated DNA Technologies).

In one embodiment, the looped primer comprises an internal quencher (e.g., Zen® or Onyx A®) and a 5' fluorophore (e.g., Yakima Yellow® or HEX).

In some embodiments, the first sensor molecule and the second sensor molecule can form a complex that generates a detectable light signal.

The first and the second clamping oligonucleotides are complementary to each other, so they can bind to each other. The first clamping oligonucleotide, the spacing oligonucleotide and the second clamping oligonucleotide can form a hairpin structure at a temperature below the melting temperature ($T_m$) of the first and second clamping oligonucleotides.

In some embodiments, the melting temperature ($T_m$) of the first and second clamping oligonucleotides is above 60° C. In some embodiments, the melting temperature ($T_m$) of the first and second clamping oligonucleotides is above 65° C. In some embodiments, the melting temperature ($T_m$) of the first and second clamping oligonucleotides is above 70° C. In some embodiments, the melting temperature ($T_m$) of the first and second clamping oligonucleotides is above 80° C. In some embodiments, the melting temperature ($T_m$) of the first and second clamping oligonucleotides is from 70 to 80° C. In some embodiments, the melting temperature ($T_m$) of the first and second clamping oligonucleotides is from 72.5 to 77.5° C. In some embodiments, the melting temperature ($T_m$) of the first and second clamping oligonucleotides is about 75° C. In some embodiments, the melting temperature ($T_m$) of the first and second clamping oligonucleotides is below 60° C. In some embodiments, the melting temperature ($T_m$) of the first and second clamping oligonucleotides is from 60 to 65° C.

In some embodiments, the melting temperature ($T_m$) of the first and second clamping oligonucleotides is 10° C. higher than the extension temperature of the assay using a strand displacing polymerase. In some embodiments, the melting temperature is lower than, equal to, or any amount higher than the extension temperature of the assay.

When the $T_m$ is lower than the reaction's extension temperature, real time detection can be replaced with end-point detection (cooling the reaction to near or below the $T_m$ of the clamping sequence), and there may be no inhibition of the reaction, even when using Loop-de-Loop primers at full strength (100/6 substitution).

Where the $T_m$ is equal to the reaction's extension temperature, real time detection can be still viable, but there may be higher background fluorescence until cooling the reaction for an endpoint determination.

When the $T_m$ is greater than the reaction's extension temperature, real time detection can be a dominant mode of operation, and there will be minimal background fluorescence.

In some embodiments, the first clamping oligonucleotide and the second clamping oligonucleotide are from 3 to 10-nucleotide long. In some embodiments, the first clamping oligonucleotide and the second clamping oligonucleotide are from 3 to 7-nucleotide long. In some embodiments, the first clamping oligonucleotide and the second clamping oligonucleotide are 6-nucleotide long. In typical embodiments, the first clamping oligonucleotide and the second clamping oligonucleotide have the same length.

In some embodiments, the spacing oligonucleotide is from 5 to 35-nucleotide long. In some embodiments, the spacing oligonucleotide is from 10 to 20-nucleotide long. In some embodiments, the spacing oligonucleotide is from 13 to 18-nucleotide long. In some embodiments, the spacing oligonucleotide is 13-nucleotide long.

In some embodiments, the first clamping oligonucleotide, the spacing oligonucleotide, and the second clamping oligonucleotide together are from 15 to 35-nucleotide long. In some embodiments, the first clamping oligonucleotide, the spacing oligonucleotide, and the second clamping oligonucleotide together are from 20 to 30-nucleotide long. In some embodiments, the first clamping oligonucleotide, the spacing oligonucleotide, and the second clamping oligonucleotide together are from 23 to 28-nucleotide long.

The looped primer can comprise (i) a nucleobase selected from adenine, guanine, cytosine, thymine, and uracil, (ii) a locked nucleic acid, (iii) a 2' O-methyl RNA base, (iv) a phosphorothioated DNA base, (v) a phosphorothioated RNA base, (vi) a phosphorothioated 2'-O-methyl RNA base, or (vii) a combination thereof. The first clamping oligonucleotide, the spacing oligonucleotide, and the second clamping oligonucleotide comprise (i) a nucleobase selected from adenine, guanine, cytosine, thymine, and uracil, (ii) a locked nucleic acid, (iii) a 2' O-methyl RNA base, (iv) a phosphorothioated DNA base, (v) a phosphorothioated RNA base, (vi) a phosphorothioated 2'-O-methyl RNA base, or (vii) a combination thereof.

In some embodiments, the looped primer further comprises a first additional oligonucleotide at 5' end of the looped primer. In some embodiments, the looped primer further comprises a second additional oligonucleotide between the first sensor molecule and the first clamping oligonucleotide. In some embodiments, the first or the second additional oligonucleotide is a barcode sequence.

In some embodiments, the looped primer comprises additional a barcode sequence, a probe sequence or other sequence further to the 5' end of the looped primer. The additional sequence can comprise a nucleobase or a modification thereof.

In some embodiments, the target sequence is specific to a pathogen genome. In some embodiments, the target sequence is specific to *Chlamydia trachomatis*. In some embodiments, the target sequence is from orf8 or cds2. Specifically, the target binding site can have a sequence of SEQ ID NO: 15.

In some embodiments, the target sequence is specific to *Neisseria gonorrhoeae*. In some embodiments, the target sequence is from porA or glnA. Specifically, the target binding site can have a sequence of SEQ ID NO: 5 or 7.

In some embodiments, the target sequence is specific to *Homo sapiens*. In some embodiments, the target sequence is from tbc1d3. Specifically, the target binding site can have a sequence of SEQ ID NO: 22.

6.4. Primer Mixture for Loop-De-Loop Amplification

In another aspect, the present invention provides a primer mixture for loop-de-loop amplification. The primer mixture comprises the looped primer provided herein.

In some embodiments, the primer mixture comprises one looped primer. In some embodiments, the primer mixture comprises more than one looped primers. When it contains more than one looped primers, primers in the mixture can bind to a single target sequence or multiple target sequences. In some embodiments, a plurality of looped primers are designed to detect target sequences from multiple sources. For example, a mixture can comprise a plurality of looped primers designed to detect target sequences from a plurality of pathogens.

The primer mixture can further comprise additional primers for the amplification reaction. For example, the primer mixture can further comprise (i) a forward inner primer (FIP), (ii) a backward inner primer (BIP), (iii) a forward primer (F3), and a backward primer (B3), wherein the FIP, the BIP, the F3, and the B3 bind to six different binding sites on the target sequence. In some embodiments, the primer mixture further comprises (i) a loop forward primer (LF) and (ii) a loop backward primer (LB), wherein the LF and the LB bind to two different binding sites on the target sequence. In some embodiments, one of the additional primers, e.g., the FIP, the BIP, the F3, the B3, the LF, or the LB, binds to the first binding site, i.e., the same binding site on the target sequence as the looped primer.

In some embodiments, the primer mixture comprises one primer set. In some embodiments, a primer set comprises a looped primer for loop-de-loop amplification provided herein, (i) a forward inner primer (FIP), (ii) a backward inner primer (BIP), (iii) a forward primer (F3), and (iv) a backward primer (B3). In some embodiments, the primer set further comprises (i) a loop forward primer (LF) and (ii) a loop backward primer (LB).

In some embodiments, a primer set comprises a looped primer for loop-de-loop amplification provided herein, and three primers selected from (i) a forward inner primer (FIP), (ii) a backward inner primer (BIP), (iii) a forward primer (F3), and (iv) a backward primer (B3). In some embodiments, a primer set comprises a looped primer, BIP, F3 and B3. In some embodiments, a primer set comprises a looped primer, FIP, F3 and B3. In some embodiments, a primer set comprises a looped primer, FIP, BIP and B3. In some embodiments, a primer set comprises a looped primer, FIP, BIP and F3.

In some embodiments, a primer set comprises a looped primer for loop-de-loop amplification provided herein, and five primers selected from (i) a forward inner primer (FIP), (ii) a backward inner primer (BIP), (iii) a forward primer (F3), (iv) a backward primer (B3), (v) a loop forward primer (LF) and (vi) a loop backward primer (LB). In some embodiments, a primer set comprises a looped primer, BIP, F3, B3, LF and LB. In some embodiments, a primer set comprises a looped primer, FIP, F3, B3, LF and LB. In some embodiments, a primer set comprises a looped primer, FIP, BIP, B3, LF and LB. In some embodiments, a primer set comprises a looped primer, FIP, BIP, F3, LF and LB. In some embodiments, a primer set comprises a looped primer, FIP, BIP, F3, B3, and LF. In some embodiments, a primer set comprises a looped primer, FIP, BIP, F3, B3 and LB.

In some embodiments, the primer mixture comprises two primer sets. In some embodiments the primer mixture comprises three primer sets. In some embodiments, the primer mixture comprises four or five primer sets.

In some embodiments, each primer set is for amplifying a unique target sequence. In some embodiments, the primer mixture comprises two or more primer sets for amplifying the same target sequence. In some embodiments, the primer mixture comprises two or more looped primers binding to the same binding site on the same target sequence.

The looped primer can be mixed with the additional primers at any ratio optimized for the amplification reaction. In some embodiments, the FIP binds to the first binding site, and the ratio between the amounts of the FIP and the looped primer in the primer mixture is 0:1, 1:1, 2:1, 3:1, 4:1, 5:1, 6:1, 7:1, 8:1, or 9:1. In some embodiments, the BIP binds to the first binding site, and the ratio between the amounts of the BIP and the looped primer in the primer mixture is 0:1, 1:1, 2:1, 3:1, 4:1, 5:1, 6:1, 7:1, 8:1, or 9:1. In some embodiments, the LF binds to the first binding site, and the ratio between the amounts of the LF and the looped primer in the primer mixture is 0:1, 1:1, 2:1, 3:1, 4:1, 5:1, 6:1, 7:1, 8:1, or 9:1. In some embodiments, the LB binds to the first binding site, and the ratio between the amounts of the LB and the looped primer in the primer mixture is 0:1, 1:1, 2:1, 3:1, 4:1, 5:1, 6:1, 7:1, 8:1, or 9:1.

In some embodiments, the primer mixture is designed to detect a target sequence specific to *Neisseria gonorrhoeae*. In some embodiments, the F3 comprises the oligonucleotide of SEQ ID NO: 1, the B3 comprises the oligonucleotide of SEQ ID NO: 2, the FIP comprises the oligonucleotide of SEQ ID NO: 3, the BIP comprises the oligonucleotide of SEQ ID NO: 4, the LF comprises the oligonucleotide of SEQ ID NO: 6, or the LB comprises the oligonucleotide of SEQ ID NO: 8. In one embodiment, the F3 comprises the oligonucleotide of SEQ ID NO: 1, the B3 comprises the oligonucleotide of SEQ ID NO: 2, the FIP comprises the oligonucleotide of SEQ ID NO: 3, the BIP comprises the oligonucleotide of SEQ ID NO: 4, the LF comprises the oligonucleotide of SEQ ID NO: 6, and the LB comprises the oligonucleotide of SEQ ID NO: 8. In some embodiments, the looped primer is the oligonucleotide of SEQ ID NO: 5 or 7.

In some embodiments, the primer mixture is designed to detect a target sequence specific to *Chlamydia trachomatis*. In some embodiments, the F3 comprises the oligonucleotide of SEQ ID NO: 9, the B3 comprises the oligonucleotide of SEQ ID NO: 10, the FIP comprises the oligonucleotide of SEQ ID NO: 11, the BIP comprises the oligonucleotide of SEQ ID NO: 12, the LF comprises the oligonucleotide of SEQ ID NO: 13, or the LB comprises the oligonucleotide of SEQ ID NO: 14. In one embodiment, the F3 comprises the oligonucleotide of SEQ ID NO: 9, the B3 comprises the oligonucleotide of SEQ ID NO: 10, the FIP comprises the oligonucleotide of SEQ ID NO: 11, the BIP comprises the oligonucleotide of SEQ ID NO: 12, the LF comprises the oligonucleotide of SEQ ID NO: 13, and the LB comprises the oligonucleotide of SEQ ID NO: 14. In some embodiments, the looped primer is the oligonucleotide of SEQ ID NO: 15.

In some embodiments, the primer mixture is designed to detect a target sequence specific to *Homo sapiens*. In some embodiments, the F3 comprises the oligonucleotide of SEQ ID NO: 16, the B3 comprises the oligonucleotide of SEQ ID NO: 17, the FIP comprises the oligonucleotide of SEQ ID NO: 18, the BIP comprises the oligonucleotide of SEQ ID NO: 19, the LF comprises the oligonucleotide of SEQ ID NO: 20, or the LB comprises the oligonucleotide of SEQ ID NO: 21. In one embodiment, the F3 comprises the oligonucleotide of SEQ ID NO: 16, the B3 comprises the oligonucleotide of SEQ ID NO: 17, the FIP comprises the oligonucleotide of SEQ ID NO: 18, the BIP comprises the oligonucleotide of SEQ ID NO: 19, the LF comprises the oligonucleotide of SEQ ID NO: 20, and the LB comprises the oligonucleotide of SEQ ID NO: 21. In some embodiments, the looped primer is the oligonucleotide of SEQ ID NO: 22.

In some embodiments, the primer mixture is designed to detect a target sequence specific to a virus. In some embodiments, the virus is SARS-CoV-2.

In some embodiments, the primer mixture provided herein are further combined for detection of multiple target sequences. In some embodiments, the multiple target sequences are specific to different organisms. For example, the multiple target sequences are specific to different pathogens.

Accordingly, in some embodiments, the primer mixture further comprises a second looped primer, wherein the second looped primer comprises:

a third sensor molecule;
a third clamping oligonucleotide;
a second spacing oligonucleotide;
a fourth clamping oligonucleotide,
    wherein the third clamping oligonucleotide, the second spacing oligonucleotide and the fourth clamping oligonucleotide can form a hairpin structure at a temperature below the melting temperature ($T_m$) of the third and fourth clamping oligonucleotides;
a fourth sensor molecule,
    wherein the third sensor molecule and the fourth sensor molecule are a second biosensor pair, and the second biosensor pair differs from the first biosensor pair; and
a second primer sequence complementary to a first binding site on a second target sequence.

In some embodiments, the third clamping oligonucleotide is complementary to the fourth clamping oligonucleotide. In some embodiments, the third clamping oligonucleotide can bind to the fourth clamping oligonucleotide but is not completely complementary to the fourth clamping oligonucleotide.

In some embodiments, the primer mixture further comprises (i) a second forward inner primer (SFIP), (ii) a second backward inner primer (SBIP), (iii) a second forward primer (SF3), and a second backward primer (SB3), wherein the SFIP, the SBIP, the SF3, and the SB3 bind to six different binding sites on the second target sequence. In some embodiments, the primer mixture further comprises (i) a second loop forward primer (SLF) and (ii) a second loop backward primer (SLB), wherein the SLF and the SLB bind to two different binding sites on the second target sequence.

In some embodiments, the primer mixture further comprises a third looped primer, wherein the third looped primer comprises:

a fifth sensor molecule;
a fifth clamping oligonucleotide;
a third spacing oligonucleotide;
a sixth clamping oligonucleotide,
    wherein the fifth clamping oligonucleotide, the third spacing oligonucleotide and the sixth clamping oligonucleotide can form a hairpin structure at a temperature below the melting temperature ($T_m$) of the fifth and sixth clamping oligonucleotides;
a sixth sensor molecule,
    wherein the fifth sensor molecule and the sixth sensor molecule are a third biosensor pair, and the third biosensor pair differs from the first biosensor pair and the second biosensor pair; and
a second primer sequence complementary to a first binding site on a third target sequence In some embodiments, the fifth clamping oligonucleotide is complementary to the sixth clamping oligonucleotide. In some embodiments, the fifth clamping oligonucleotide binds to the sixth clamping oligonucleotide, but the fifth clamping oligonucleotide is not completely complementary to the sixth clamping oligonucleotide.

In some embodiments, the primer mixture further comprises (i) a third forward inner primer (TFIP), (ii) a third backward inner primer (TBIP), (iii) a third forward primer (TF3), and a third backward primer (TB3), wherein the TFIP, the TBIP, the TF3, and the TB3 bind to six different binding sites on the third target sequence.

In some embodiments, the primer mixture comprises (i) a third loop forward primer (TLF) and (ii) a third loop backward primer (TLB), wherein the TLF and the TLB bind to two different binding sites on the third target sequence.

In some embodiments, the primer mixture comprises two, three, four, five, or six looped primers. When the primer mixture comprises two or more looped primers, each looped primer can comprise a unique biosensor pair, each providing a unique signal for detection. In some embodiments, each biosensor pair provides a unique visual signal (e.g., a color) for detection. In some embodiments, each biosensor pair comprises a unique dye molecule.

In some embodiments, two or more looped primers in the primer mixture comprise an identical biosensor pair. In some embodiments, two or more looped primers in the primer mixture are labeled with FAM. In some embodiments, two different looped primers in the primer mixture are labeled with FAM.

In some embodiments, the primer mixture provided herein is lyophilized. The dried primer mixture can comprise any of the looper primer or the primer mixture described herein. In some embodiments, a primer mixture comprising two or more looped primers is lyophilized. In some embodiments, a primer mixture is in the form of lyophilized beads.

6.5. Kit for Loop-De-Loop Amplification

In another aspect, a kit for loop-de-loop amplification is provided. The kit can comprise any of the looped primer or the primer mixture provided herein.

In some embodiments, a kit comprises one primer set. In some embodiments, the primer set comprises a looped primer for loop-de-loop amplification provided herein, (i) a forward inner primer (FIP), (ii) a backward inner primer (BIP), (iii) a forward primer (F3), and a backward primer (B3). In some embodiments, the primer set further comprises (i) a loop forward primer (LF) and (ii) a loop backward primer (LB).

In some embodiments, the kit comprises two primer sets. In some embodiments the kit comprises three primer sets. In some embodiments, the kit comprises four or five primer sets.

In some embodiments, the kit comprises a plurality of primer sets contained in a single container. In some embodiments, the kit comprises a plurality of primer sets, wherein each primer set is individually contained in a separate container.

In some embodiments, the kit further comprises a polymerase. In some embodiments, the polymerase is a strand-displacing DNA polymerase. In some embodiments, the polymerase is a *Bacillus stearothermophilus* polymerase. In some embodiments, the polymerase is Bst 2.0 WarnStart® DNA Polymerase (available from NEB). In some embodiments, the kit further comprises other reaction enzyme, e.g., a reverse transcriptase. In some embodiments, the reverse transcriptase is WarmStart® RTx Reverse Transcriptase (available from NEB). In some embodiments, the kit further comprises an RNase inhibitor. In some embodiments, the RNase inhibitor is a porcine or murine RNase inhibitor.

In some embodiments, the kit further comprises a reagent for the amplification reaction. In some embodiments, the reagent comprises dNTPs, MgSO4, and a buffer. In some embodiments, the buffer comprises a surfactant. In some embodiments, the buffer comprises 1, 2, 3, 4, 5, 6, 7, 8, 9, or 10% of Tween-20. In some embodiments, the reagent comprises trehalose. In some embodiments, the reagent comprises sucrose. In some embodiments, the reagent comprises polymers for stabilization. The amplification reagent can be selected and optimized depending on the polymerase.

In some embodiments, the kit comprises a mixture comprising dNTPs, MgSO4, a buffer, one or more primer sets for loop-de-loop amplification, and polymerase. In some embodiments, the kit comprises a mixture comprising dNTPs, one or more primer sets for loop-de-loop amplification, polymerase, reverse transcriptase, and RNase inhibitor.

In some embodiments, the mixture is in a liquid form. In some embodiments, the mixture is in a dried form. In some embodiments, the mixture is formulated into lyophilized beads or pellets.

In some embodiments, the kit further comprises a device for the amplification reaction. In some embodiments, the kit comprises a device for looped-mediated isothermal amplification.

In some embodiments, the kit further comprises a reaction tube for running the amplification reaction. In some embodiments, the kit further comprises a component for filtration or purification of a sample before the amplification reaction.

In some embodiments, the kit is for diagnosis of a disease of infection. In some embodiments, the kit is for diagnosis of pathogenic infection, such as *Chlamydia trachomatis* and *Neisseria gonorrhoeae*. In some embodiments, the kit is used for determination of single nucleotide polymorphisms (SNPs) and point mutations. In some embodiments, the kit is used for determination of a mutant genotype. In some embodiments, the kit is used for determination of a mutant genotype associated with a drug-resistant phenotype. For example, a drug resistant marker, e.g., ceftriaxone/cefixime resistance marker, quinolone (ciprofloxacin) resistance marker, macrolide resistance marker (azithromycin), can be detected.

6.6. Loop-De-Loop Amplification Methods

In another aspect, loop-de-loop amplification methods are provided. The method can comprise the steps of:

providing a sample;

adding (i) the primer, the primer mixture, or a reconstituted primer mixture obtained by rehydrating the dried primer mixture provided herein, and (ii) a polymerase to the sample, thereby generating a reaction mixture; and incubating the reaction mixture at 50-85° C.

The reaction temperature can be adjusted depending on the polymerase and the target sequences. In some embodiments, the incubation is performed at 50-70° C. In some embodiments, the incubation is performed at 55-70° C. In some embodiments, the incubation is performed at 60-65° C. In some embodiments, the incubation is performed at 62-65° C. In some embodiments, the incubation is performed at 60, 61, 62, 63, 64, or 65° C.

In some embodiments, the method further comprises the step of detecting a signal from the reaction mixture. In some embodiments, the method comprises the step of detecting a fluorescence signal. In some embodiments, the method comprises the step of detecting change of color or turbidity. In some embodiments, the method comprises the step of detecting a non-visual signal. In some embodiments, the step of detecting is performed during the step of incubation. In some embodiments, the step of detecting is performed after completion of the step of incubation. In some embodiments, the signal is detected in real time. In some embodiments, the signal is recorded in real time and analyzed after completion of the step of incubation.

In some embodiments, the method further comprises the step of preparing a sample for loop-de-loop amplification. In some embodiments, the step of preparing a sample comprises interacting RNA molecules with a reverse transcriptase, thereby generating the sample comprising DNA molecules. In some embodiments, the step of preparing a sample further comprises preheating the sample or reaction mixture containing RNA molecules before interacting with the reverse transcriptase.

In some embodiments, a sample for loop-de-loop amplification comprises purified polynucleotide molecules. In some embodiments, the sample comprises purified RNA, purified DNA, whole SARS-CoV-2 virus, whole human cells, saliva or nasal swab, or nasal or nasopharyngeal swab. In some embodiments, the sample comprises genomic DNA, synthetic DNA, whole bacteria or whole human cells from vaginal swab. In some embodiments, a sample for loop-de-loop amplification is a crude sample. In some embodiments, a sample for loop-de-loop amplification is a purified sample.

In some embodiments, more than one types of signals are detected. In some embodiments, multiple fluorescence or other visual signals are detected. In some embodiments, multiple signals are detected to determine presence or absence of multiple target sequences. In some embodiments, multiple signals are detected to confirm presence or absence of a single target sequence. In some embodiments, multiple signals are detected to provide additional sensitivity and specificity to the method.

For amplification of the target sequence, various amplification methods known in the art can be used.

In typical embodiments, loop mediated isothermal amplification ("LAMP") is used for loop-de-loop amplification of target nucleic acid. LAMP is an isothermal DNA amplification method that relies on the strand displacing activity of an enzyme known as a polymerase, which adds nucleotide bases to an extending DNA or RNA strand in a base-specific manner to form double stranded nucleic acids with complementary sequences. In isothermal amplification methods, strand displacing polymerases, such as that from the *Geobacillus stearothermophilus* bacteria (Bst polymerase and its variants), displace one strand of a double stranded DNA as they polymerize a complementary strand, and therefore do not require thermal cycling.

The LAMP method can use 4 different primers (F3, B3, inner forward primer or FIP, and inner backward primer or BIP) that are specifically designed to recognize 6 distinct regions of a target DNA sequence. 2 additional "loop" primers may be added to improve the speed of the reaction. The primers' concentrations in a reaction mixture may vary, but are typically set to 1.6 µM for FIP and BIP primers, 0.8 µM for forward and backward loop primers (LF, LB), and 0.2 µM for F3 and B3 primers. In some embodiments of the LAMP method, 5 primers may be utilized (using only 1 of the 2 possible LAMP primers). The LAMP reaction proceeds at a constant temperature (around 65° C.) using a strand displacement reaction. The amplification of the target and detection may be completed in one step, by incubating the sample, primers, DNA polymerase with strand displacement activity, buffers, and substrates at a constant temperature. A typical mixture composition for LAMP contains the following reagents: 20 mM Tris-HCL, 10 mM $(NH_4)_2SO_4$, 50 mM KCl, 8 mM MgSO4, 0.1% Tween® 20, 1.4 mM dNTPs, 0.32 U/µL Bst polymerase, primers at the aforementioned concentrations, and water, with pH adjusted to 8.8 at 20° C. Reaction volumes are typically between 5 µL and 50 µL. The temperature of the reaction is optimized for the specific enzyme and primers used, and the reaction proceeds for 5 to 60 minutes. LAMP is highly sensitive, specific, and efficient.

LAMP relies on at least 4 primers recognizing 6 target sites (e.g., F3, B3, FIP and BIP) to amplify specific DNA or RNA targets (RNA targets first require reverse transcription into DNA). If loop primers (e.g., LF and LB) are included, a total of 8 unique sites in the target nucleic acid are recognized by 6 primers. In various embodiments provided herein, one of the total 8 unique sites can be recognized by the looped primer described herein. If the target is present in a sample, the amplification reaction can occur, and provide large quantities of DNA.

The novel loop-de-loop method described herein may be applied to other isothermal amplification methods beyond LAMP. Numerous isothermal amplification methods have been created to address the temperature cycling dependency of polymerase chain reaction (PCR). Although these methods can vary considerably, they all share some features in common. For example, because the DNA strands are not heat denatured, all isothermal methods rely on an alternative approach to enable primer binding and initiation of the amplification reaction. Once the reaction is initiated, the polymerase must also displace the strand that is still annealed to the sequence of interest. Isothermal methods typically employ strand-displacement activity of a DNA polymerase for separating duplex DNA. Polymerases with this ability include Klenow Fragment (3'-5' exo-), Bsu large fragment, and phi29 for moderate temperature reactions (25-40° C.), and the large fragment of Bst DNA polymerase for higher temperature (50-65° C.) reactions. To detect RNA species a reverse transcriptase compatible with the temperature of the reaction is added to maintain the isothermal nature of the amplification. In addition to the strand displacement mechanism to separate dsDNA, isothermal methods can require enzymes or primer design to avoid initial denaturation requirements for initiation.

As discussed above, Loop-mediated isothermal amplification (LAMP) uses 4-6 primers recognizing 6-8 distinct regions of target DNA. A strand-displacing DNA polymerase initiates synthesis and 2 of the primers form loop structures to facilitate subsequent rounds of amplification. LAMP is rapid, sensitive, and amplification is so extensive that LAMP is well-suited for field diagnostics. Loop-de-Loop primers may be used for single or any combination or the inner and or loop primers.

Strand displacement amplification (SDA) relies on a strand-displacing DNA polymerase, typically Bst DNA Polymerase, Large Fragment or Klenow Fragment (3'-5' exo-), to initiate at nicks created by a strand-limited restriction endonuclease or nicking enzyme at a site contained in a primer. SDA requires 1 forward and 1 reverse primer, as well as 1 bumping forward primer and 1 bumping reverse primer. The nicking site is regenerated with each polymerase displacement step, resulting in exponential amplification. SDA is typically used in clinical diagnostics. Existing fluorescence monitoring techniques exist for SDA (Nadeau et al., Real-Time, Sequence-specific detection of nucleic acids during strand displacement amplification, 276 m 2 177-187 (1999)), but rely upon the action of a restriction endonuclease enzyme to generate the fluorescence. Either the forward or reverse SDA primers could be adapted for use with the loop-de-loop method, which would not require the location of a cut site between a fluorophore and quencher pair. The cut site would exist next to the clamping sequence of the loop-de-loop primer, toward the 3' end of the primer, so that fluorescence is produced upon complete extension of the primer's 5' end by a polymerase on the complementary strand, prior to primer cleavage by a restriction endonuclease.

Helicase-dependent amplification (HDA) employs the double-stranded DNA unwinding activity of a helicase to separate strands, enabling primer annealing and extension by a strand-displacing DNA polymerase. Like PCR, this system requires only two primers, 1 forward primer and 1 reverse primer. HDA has been employed in several diagnostic devices and FDA-approved tests. Either primer in HDA can be adapted for use with the loop-de-loop method to produce real-time, closed tube monitoring of reaction in real time. In HDA, the helicase enzyme can open the loop structure of the loop-de-loop primer, which can be stabilized by single stranded binding protein, and then turned into a double-stranded, fluorescent amplicon by a DNA polymerase.

Nicking enzyme amplification reaction (NEAR) employs a strand-displacing DNA polymerase initiating at a nick created by a nicking enzyme, rapidly producing many short nucleic acids from the target sequence. This process is extremely rapid and sensitive, enabling detection of small target amounts in minutes. NEAR is commonly used for pathogen detection in clinical and biosafety applications. Either forward or reverse primers for NEAR can use the Loop-de-loop method to generate real-time fluorescence via extension of the loop by the strand displacing DNA polymerase.

6.7. Methods of Use

Loop-de-loop amplification method provided herein can be used to detect a target sequence from various sources. For example, it can be used to detect a target sequence specific to a viral genome, a bacterial genome, an archaea genome, a plant genome, an animal genome, a protist genome, a prokaryotic genome, or a eukaryotic genome. In some embodiments, the method is used to detect an RNA (e.g., a positive sense RNA, a negative sense RNA), or DNA. In some embodiments, the method is used to detect a synthetically generated target sequence.

In some embodiments, loop-de-loop method is used for detection of DNA specific to a pathogen. In some embodiments, the pathogen is a virus, bacteria, fungi, protozoa or worm. In some embodiments, loop-de-loop method is used to detect a pathogen associated with STD. In some embodiments, the pathogen is *Chlamydia trachomatis*. In some embodiments, the pathogen is *Neisseria gonorrhoeae*. In some embodiments, the pathogen is SARS-CoV-2.

In some embodiments, loop-de-loop method is used for diagnosis of infection. In some embodiments, loop-de-loop method is used for determination of a mutant genotype. In some embodiments, loop-de-loop method is used for determination of a mutant genotype associated with a drug-resistant phenotype. For example, a drug resistant marker, e.g., ceftriaxone/cefixime resistance marker, quinolone (ciprofloxacin) resistance marker, macrolide resistance marker (azithromycin), can be detected.

In some embodiments, loop-de-loop method is used for determination of a single nucleotide polymorphism (SNPs). In some embodiments, loop-de-loop method is used for determination of a mutation.

In some embodiments, loop-de-loop method is used for detection of a single target. In some embodiments, loop-de-loop method is used for detection of more than one targets. In some embodiments, loop-de-loop method is used for detection of 2, 3, 4, or 5 targets.

In some embodiments, loop-de-loop method is used for analysis or characterization of a sample. In some embodiments, loop-de-loop method is used for identifying a source of a sample. For example, loop-de-loop method is used for identifying a human sample.

The loop-de-loop method described herein can be used in analysis of various samples. In some embodiments, blood, urine, semen, tissue, or saliva sample is analyzed. In some embodiments, the sample is collected from an animal or a human patient. In some embodiments, a purified sample is analyzed. In some embodiments, a crude sample is analyzed. In some embodiments, the sample comprises purified RNA, purified DNA, whole SARS-CoV-2 virus, whole human cells, saliva or nasal swab, or mid-turbinate or nasopharyngeal swab. In some embodiments, the sample comprises genomic DNA, synthetic DNA, whole bacteria or whole human cells from vaginal swab.

6.8. EXAMPLES

The following examples are provided by way of illustration not limitation.

6.8.1. Example 1: LAMP Assay for *Chlamydia trachomatis* and *Neisseria gonorrhoeae* Using an Intercalating Dye (SYTO)

Figure 2A:
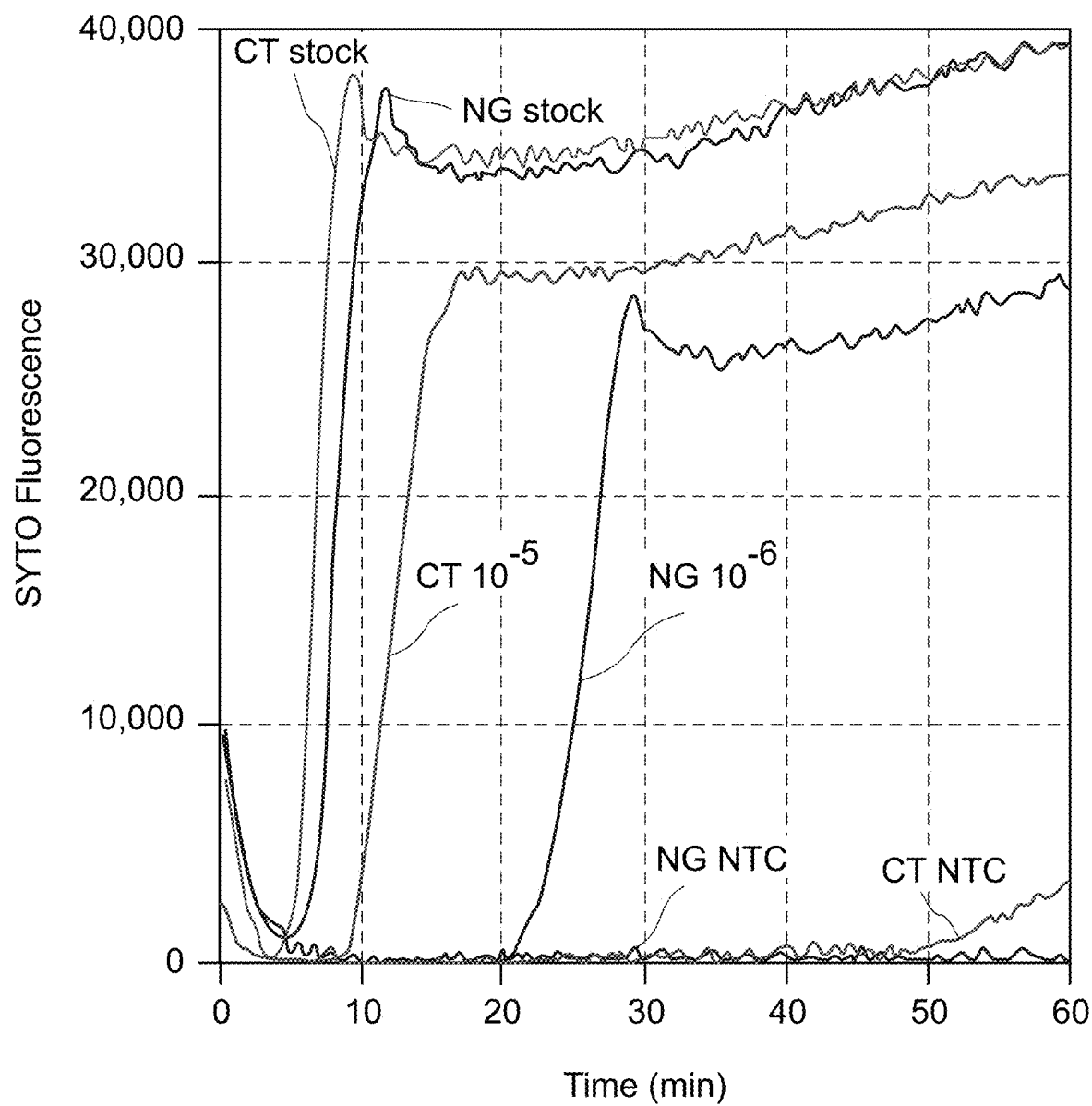

LAMP reaction mixtures were prepared to detect *Chlamydia trachomatis* genomic DNA and *Neisseria gonorrhea* genomic DNA separately. Reactions were prepared in 10 μL volumes and contained the following reagents: 20 mM Tris-HCL, 10 mM $(NH_4)_2SO_4$, 50 mM KCl, 8 mM MgSO4, 0.1% Tween® 20, 1.4 mM dNTPs, 0.32 U/μL Bst 2.0 WarmStart® polymerase, primers (SEQ ID 1-4, 6, 8-14) with FIP and BIP at 1.6 μM, LF and LB at 0.8 μM, F3 and B3 at 0.2 μM, 2.5 μM SYTO 85 intercalating dye, and water, with pH adjusted to 8.8 at 20° C. Target genomic DNA was diluted 10-fold in pH 8.0 Tris-HCL buffer from a stock solution purchased from ATCC. Target DNA or DNA-free buffer, for no template controls, was added as 1 μL into 9 μL of solution mixture within each PCR tube. The temperature of the reactions was 65° C., and the reaction was monitored via SYTO 85 fluorescence. A real-time PCR machine was used to both heat the reactions and measure fluorescence in real-time. The reaction was run for 60 minutes. The data shown in FIG. 2A depict representative curves of the real time fluorescence (arbitrary units) on the vertical axis versus time on the horizontal axis from LAMP reactions for *Chlamydia trachomatis* (Green) and *Neisseria gonorrhoeae* (Blue), monitored by intercalating dye, for 3 levels of genomic DNA target each—High (stock concentrations), Low ($10^{-5}$ dilution of stock DNA for Ct, $10^{-6}$ dilution of stock DNA for Ng), and no template controls (no DNA (NTC)).

Figure 3:
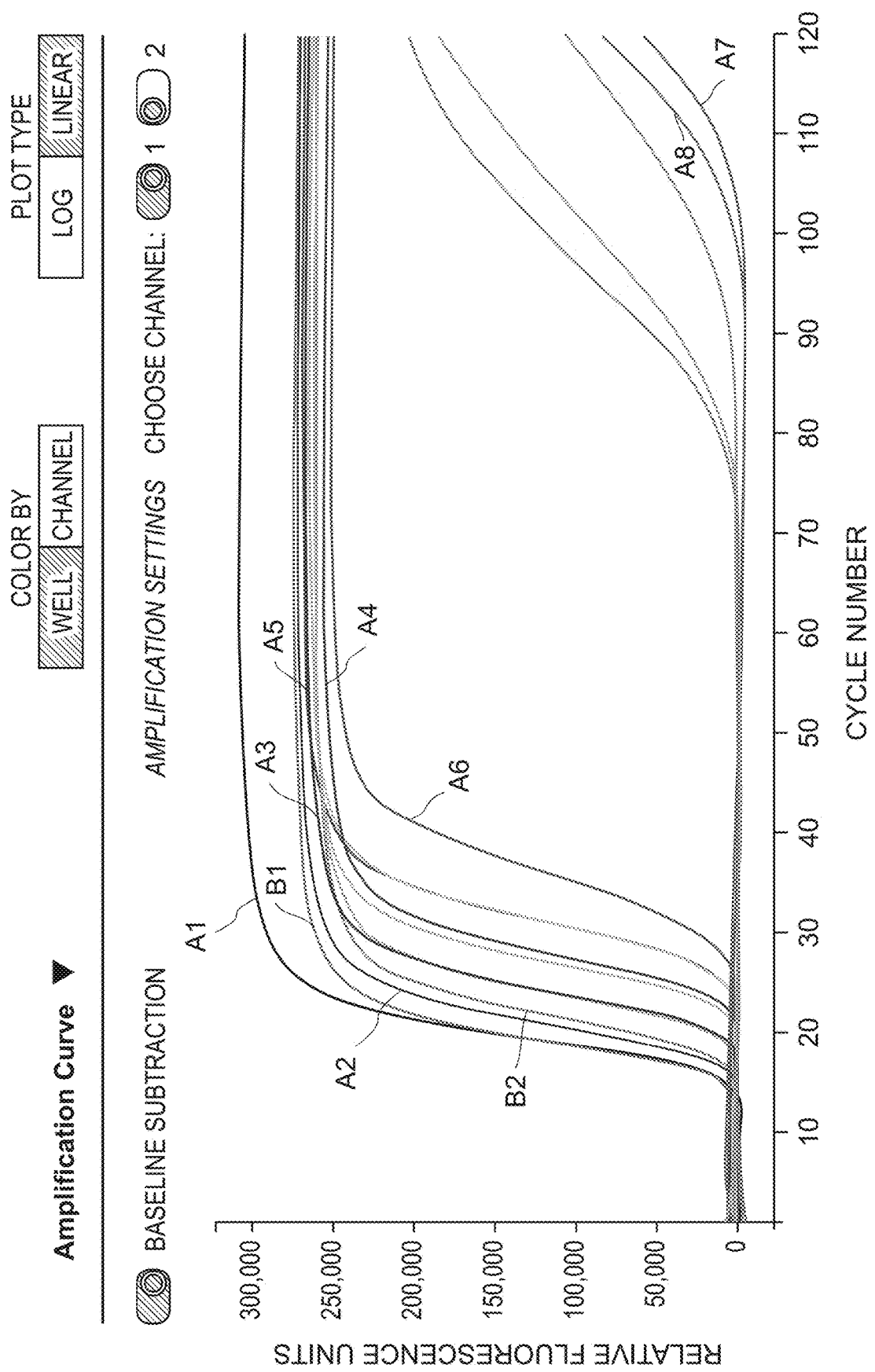

6.8.2. Example 2: Detection of *Chlamydia trachomatis* by Loop-De-Loop Amplification Loop-de-loop LAMP reaction mixtures were prepared to detect *Chlamydia trachomatis* genomic DNA. Reactions were prepared in 10 μL volumes and contained the following reagents: 20 mM Tris-HCL, 10 mM $(NH_4)_2SO_4$, 50 mM KCl, 8 mM MgSO4, 0.1% Tween® 20, 1.4 mM dNTPs, 0.32 U/μL Bst 2.0 WarmStart® polymerase, primers (SEQ ID 9-15) with FIP and BIP at 1.6 μM, LF and LF-LdL at 0.4 μM, LB at 0.8 μM, F3 and B3 at 0.2 μM, and water, with pH adjusted to 8.8 at 20° C. Quantitated target genomic DNA was diluted 10-fold or 2-fold (for finer resolution) in pH 8.0 Tris-HCL buffer from a stock solution purchased from ATCC. Target DNA dilutions or DNA-free buffer, for no template controls, were added as 1 μL into 9 μL of solution mixture within each PCR tube, and up to 20 replicates per concentration were used across a several-log concentration range to look at assay sensitivity. The temperature of the reactions was 65° C., and the reaction was monitored via FAM fluorescence given off by the loop-de-loop primer. A real-time PCR machine was used to both heat the reactions and measure fluorescence in real-time. The reaction was run for 60 minutes. The data shown in FIG. 3 depict representative curves of the real time fluorescence (arbitrary units) on the vertical axis versus time on the horizontal axis (each 'cycle' represents 30 seconds) from Loop-de-loop LAMP reactions for *Chlamydia trachomatis* for 10-fold dilutions of genomic DNA target. Assay sensitivity (limits of detection, 50% and 95% probability) was then estimated by PROBIT analysis based on endpoint determination of the assays.

| Organism | Target | Speed (min) | $LoD_{95}$ (cp/rxn) | $LoD_{50}$ (cp/rxn) |
|---|---|---|---|---|
| C. trachomatis | orf8 (cryptic plasmid) | 8-19 | 20.7 | 3.14 |

Figure 2B:
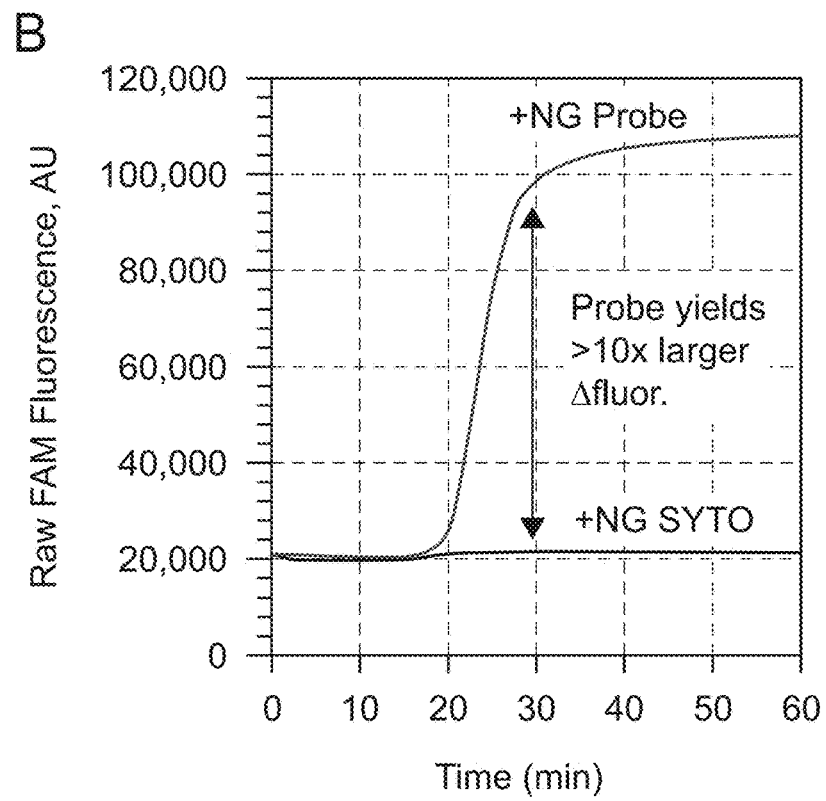
Figure 2C:
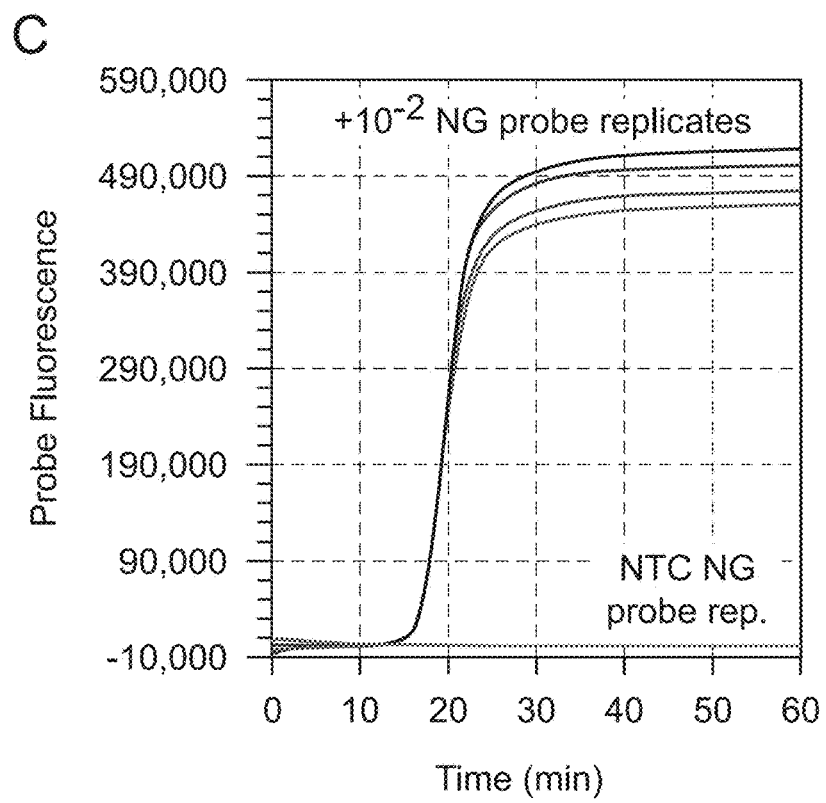
Figure 4:
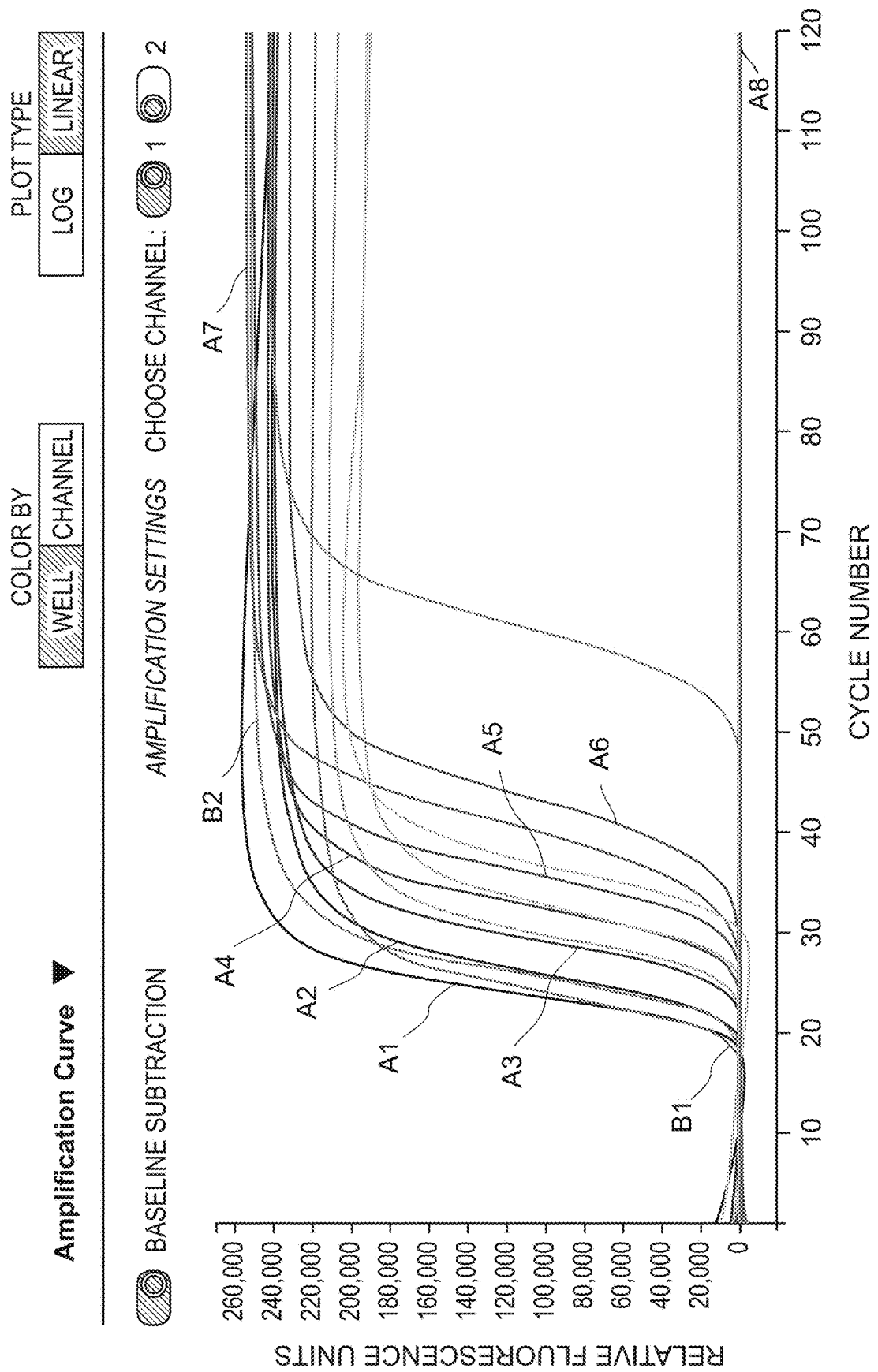
Figure 5:
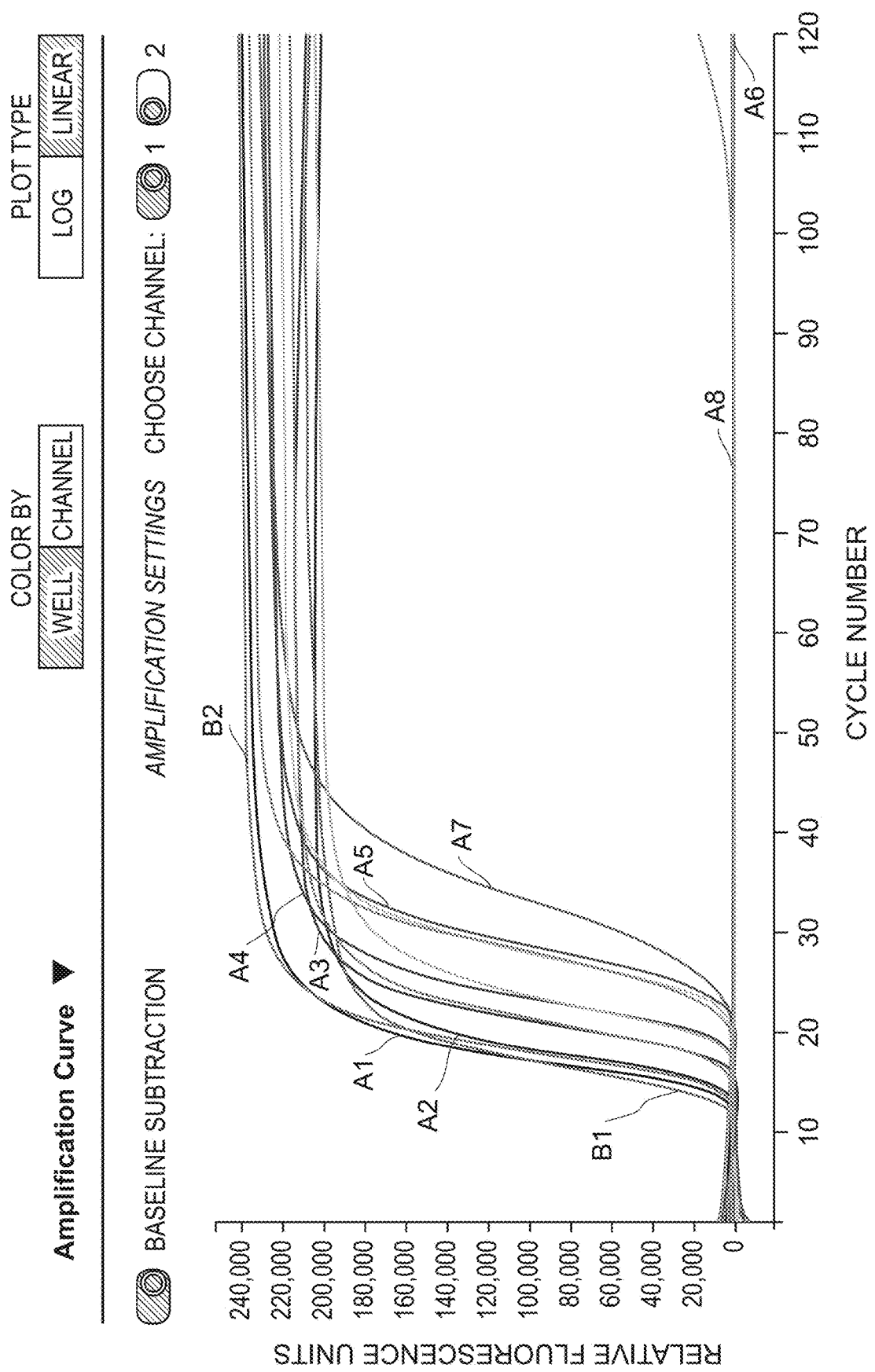
Figure 6:
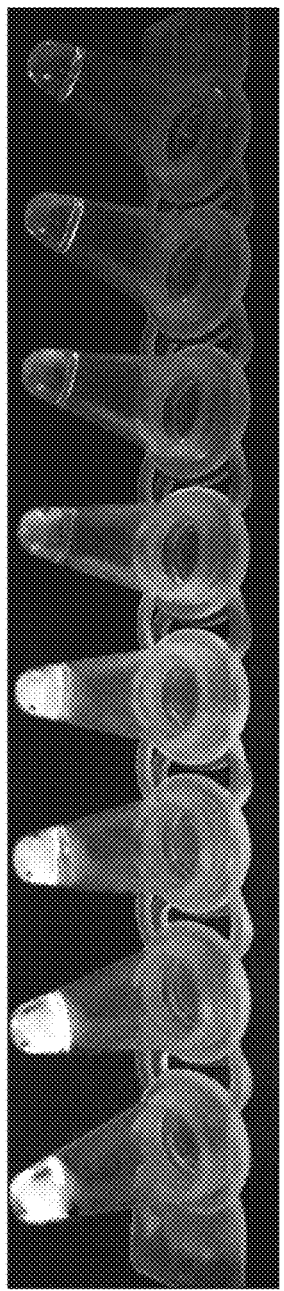

6.8.3. Example 3: Detection of *Neisseria gonorrhoeae* by Loop-De-Loop Amplification Loop-de-loop LAMP reaction mixtures were prepared to detect *Neisseria gonorrhoeae* genomic DNA. Reactions were prepared in 10 μL volumes and contained the following reagents: 20 mM Tris-HCL, 10 mM $(NH_4)_2SO_4$, 50 mM KCl, 8 mM MgSO4, 0.1% Tween® 20, 1.4 mM dNTPs, 0.32 U/µL Bst 2.0 WarmStart® polymerase, primers (SEQ ID 1-4, 6-8) with FIP and BIP at 1.6 µM, LF and LF-LdL at 0.4 µM, LB at 0.8 µM, F3 and B3 at 0.2 µM, and water, with pH adjusted to 8.8 at 20° C. Quantitated target genomic DNA was diluted 10-fold or 2-fold (for finer resolution) in pH 8.0 Tris-HCL buffer from a stock solution purchased from ATCC. Target DNA dilutions or DNA-free buffer, for no template controls, were added as 1 µL into 9 µL of solution mixture within each PCR tube, and up to 20 replicates per concentration were used across a several-log concentration range to look at assay sensitivity. The temperature of the reactions was 65° C., and the reaction was monitored via FAM fluorescence given off by the loop-de-loop primer. A real-time PCR machine was used to both heat the reactions and measure fluorescence in real-time. The reaction was run for 60 minutes. The data shown in FIG. 2B-C depict representative curves of the real time fluorescence (arbitrary units) on the vertical axis versus time on the horizontal axis from Loop-de-loop LAMP reactions for *Neisseria gonorrhoeae* for 10-fold dilutions of genomic DNA target. FIG. 2B compares the signal from the loop-de-loop assay to that of the LAMP assay performed without loop-de-loop primers and with SYTO 85 dye, as shown in FIG. 2A. The loop-de-loop assay provides for much greater signal in the case of positive amplification. In FIG. 2C, the reproducibility of the loop-de-loop assay is demonstrated, as well as the negligible background fluorescence and reduced late, spurious amplification products in no template controls. The data shown in FIG. 4 depict representative curves of the real time fluorescence (arbitrary units) on the vertical axis versus time on the horizontal axis (each 'cycle' represents 30 seconds) from Loop-de-loop LAMP reactions for *Neisseria gonorrhoeae* for 10-fold dilutions of genomic DNA target. Assay sensitivity (limits of detection, 50% and 95% probability) was then estimated from serial dilution testing results by PROBIT analysis based on endpoint determination of the assays.

| Organism | Target | Speed (min) | LoD$_{95}$ (cp/rxn) | LoD$_{50}$ (cp/rxn) |
|---|---|---|---|---|
| *N. gonorrhoeae* | porA pseudogene | 10-20 | 543 | 82.4 |

6.8.4. Example 4: Detection of *Homo sapiens* by Loop-De-Loop Amplification Loop-de-loop LAMP reaction mixtures were prepared to detect *Homo sapiens* genomic DNA. Reactions were prepared in 10 µL volumes and contained the following reagents: 20 mM Tris-HCL, 10 mM (NH$_4$)$_2$SO$_4$, 50 mM KCl, 8 mM MgSO4, 0.1% Tween® 20, 1.4 mM dNTPs, 0.32 U/µL Bst 2.0 WarmStart® polymerase, primers (SEQ ID 16-22) with FIP and BIP at 1.6 µM, LF and LF-LdL at 0.4 µM, LB at 0.8 µM, F3 and B3 at 0.2 µM, and water, with pH adjusted to 8.8 at 20° C. Quantitated target genomic DNA was diluted 10-fold or 2-fold (for finer resolution) in pH 8.0 Tris-HCL buffer from a stock solution purchased from ATCC. Target DNA dilutions or DNA-free buffer, for no template controls, were added as 1 µL into 9 µL of solution mixture within each PCR tube, and up to 20 replicates per concentration were used across a several-log concentration range to look at assay sensitivity. The temperature of the reactions was 65° C., and the reaction was monitored via FAM fluorescence given off by the loop-de-loop primer. A real-time PCR machine was used to both heat the reactions and measure fluorescence in real-time. The reaction was run for 60 minutes. The data shown in FIG. 3 depict representative curves of the real time fluorescence (arbitrary units) on the vertical axis versus time on the horizontal axis (each 'cycle' represents 30 seconds) from Loop-de-loop LAMP reactions for *Homo sapiens* for 10-fold dilutions of genomic DNA target. Assay sensitivity (limits of detection, 50% and 95% probability) was then estimated by PROBIT analysis based on endpoint determination of the assays.

| Organism | Target | Speed (min) | LoD$_{95}$ (cp/rxn) | LoD$_{50}$ (cp/rxn) |
|---|---|---|---|---|
| *H. sapiens* | tbc1d3 | 6.5-18 | 112 | 11.5 |

6.8.5. Example 5: Dried Primer Mixture for Loop-De-Loop Amplification

Figure 7:
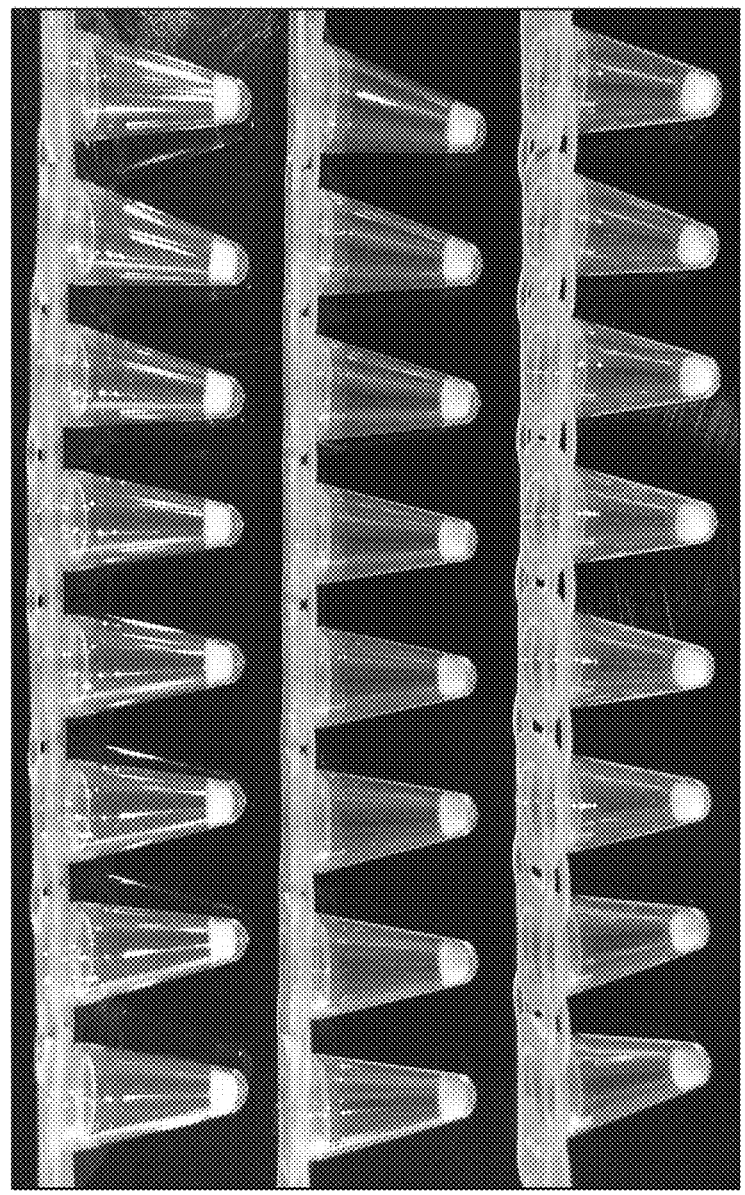
Figure 8:
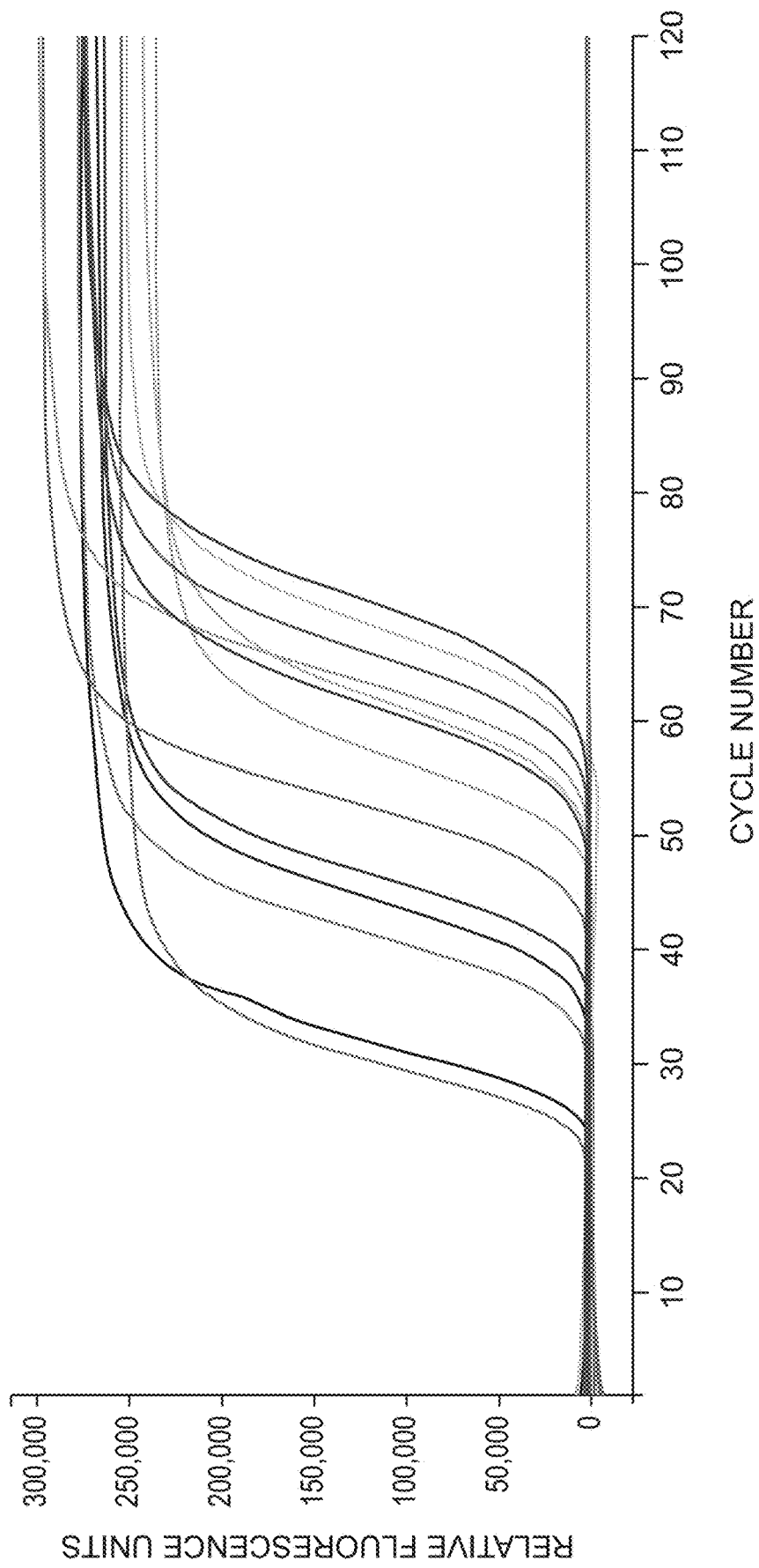

Formulation into freeze dried reagents was conducted with in-house lyophilization testing with a 5-step freeze drying protocol. Loop-de-loop LAMP reaction mixtures designed to detect *Neisseria gonorrhoeae* were prepared in 25 µL volumes per tube and aliquoted into each tube. Lyophilized mixtures contained the following reagents: 1.4 mM dNTPs, 0.32 U/µL Bst 2.0 WarmStart® polymerase as a glycerol-free formulation, primers (SEQ ID 1-4, 6-8) with FIP and BIP at 1.6 µM, LF and LF-LdL at 0.4 µM, LB at 0.8 µM, F3 and B3 at 0.2 µM, 5% trehalose, and water (up to 25 µL per reaction). The tube lids were removed for lyophilization. Tube strips were placed onto a metal shelf in a heated shelf lyophilizer unit, a standard piece of equipment in the pharmaceutical and biotechnology industry. The lyophilizer was programmed to run in 5 steps. Step 1: Condenser ON, Vacuum OFF, cool shelves and reagents to 41° F., 30 min. Condenser ON, Vacuum OFF, cool shelves and reagents to 23 F, 30 min. Step 3: Condenser ON, Vacuum OFF, cool shelves and reagents to −23 F, 2 hr. Step 4: Condenser ON, Vacuum ON, maintain shelves and reagents at −23 F, 10 hr. Step 5: Condenser ON, Vacuum ON, heat shelves and reagents to 77 F, 5 hr. Once this process was complete, the tubes were removed and capped, yielding the product shown in FIG. 7. The activity of freeze-dried assays was tested following incubation in various environmental conditions over periods of time. FIG. 8 shows representative real-time loop-de-loop LAMP assay activity of rehydrated reactions. The rehydration protocol consisted of adding 24 µL of a rehydration buffer to the dried reagents, along with 1 µL of *Neisseria gonorrhoeae* target genomic DNA. The rehydration buffer was comprised of: 20 mM Tris-HCL, 10 mM (NH$_4$)$_2$SO$_4$, 50 mM KCl, 8 mM MgSO4, 0.1% Tween® 20, and water, with pH adjusted to 8.8 at 20° C. Buffer was added to tubes, which were then re-sealed and placed directly into a real-time qPCR machine without vortexing or mixing. The temperature of the reactions was 65° C., and the reaction was monitored via FAM fluorescence given off by the loop-de-loop primer. A real-time PCR machine was used to both heat the reactions and measure fluorescence in real-time. The reaction was run for 60 minutes. The data shown in FIG. 8 depict representative curves of the real time fluorescence (arbitrary units) on the vertical axis versus time on the horizontal axis (each 'cycle' represents 30 seconds) from Loop-de-loop LAMP reactions for *Neisseria gonorrhoeae* for 10-fold dilutions of genomic DNA target. Lyophilized loop-de-loop assay speed, sensitivity, and specificity were found to be no different from freshly formulated assay speed, sensitivity, and specificity. Furthermore, the magnitude of fluorescence was unaffected by drying and rehydration, showing that the loop-de-loop method can provide shelf-stable in vitro diagnostic kits for pathogen detection.

6.8.6. Example 6: Temperature for Loop-De-Loop Amplification

Figure 9A:
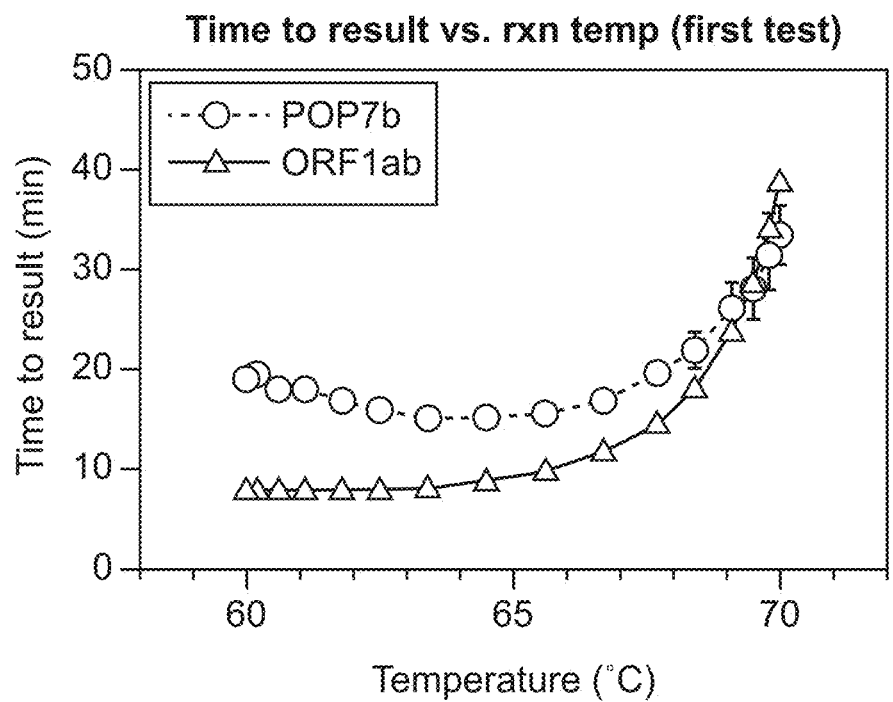
Figure 9B:
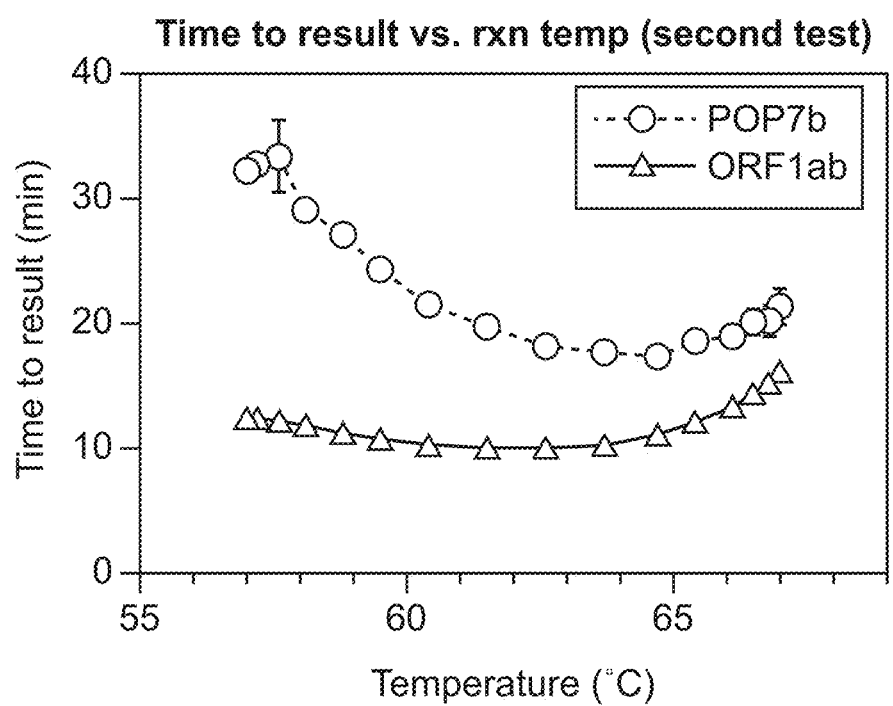
Figure 10:
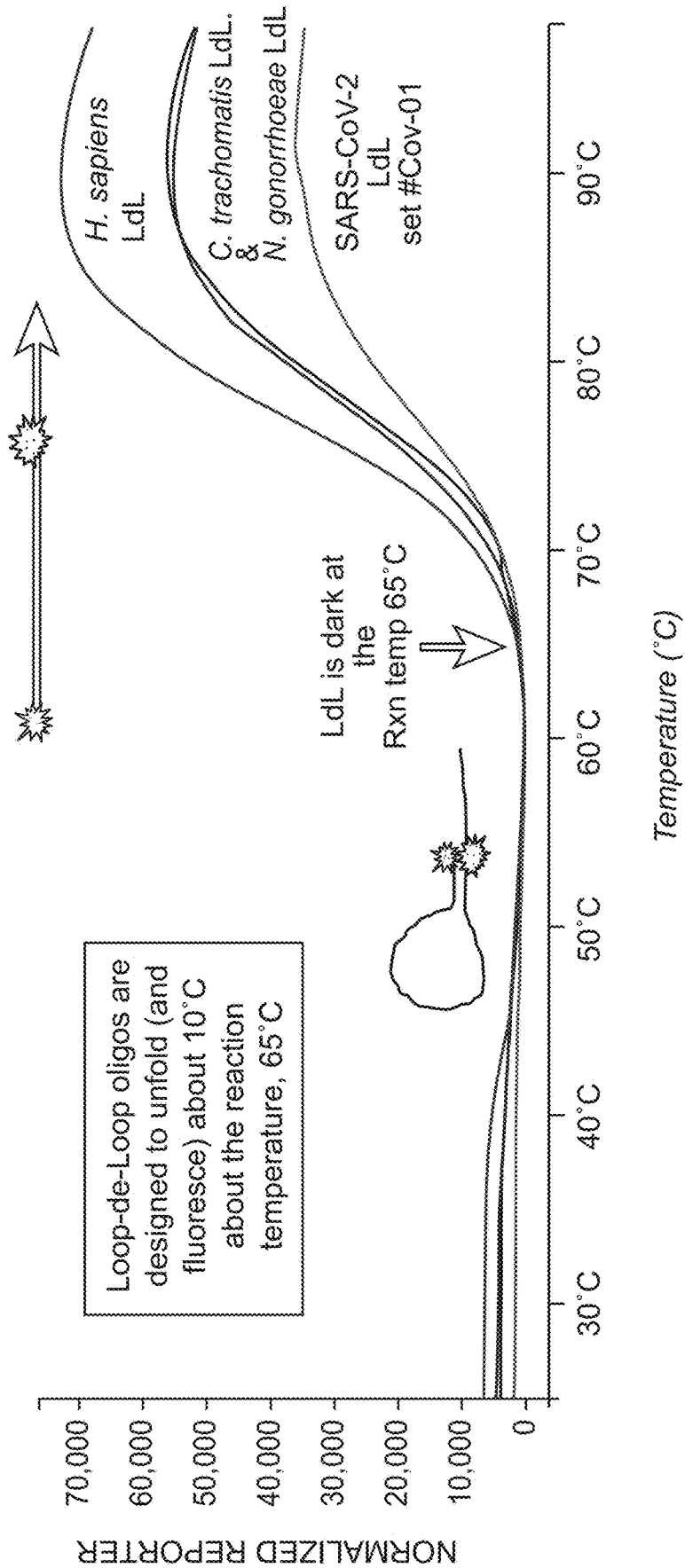
Figure 11:
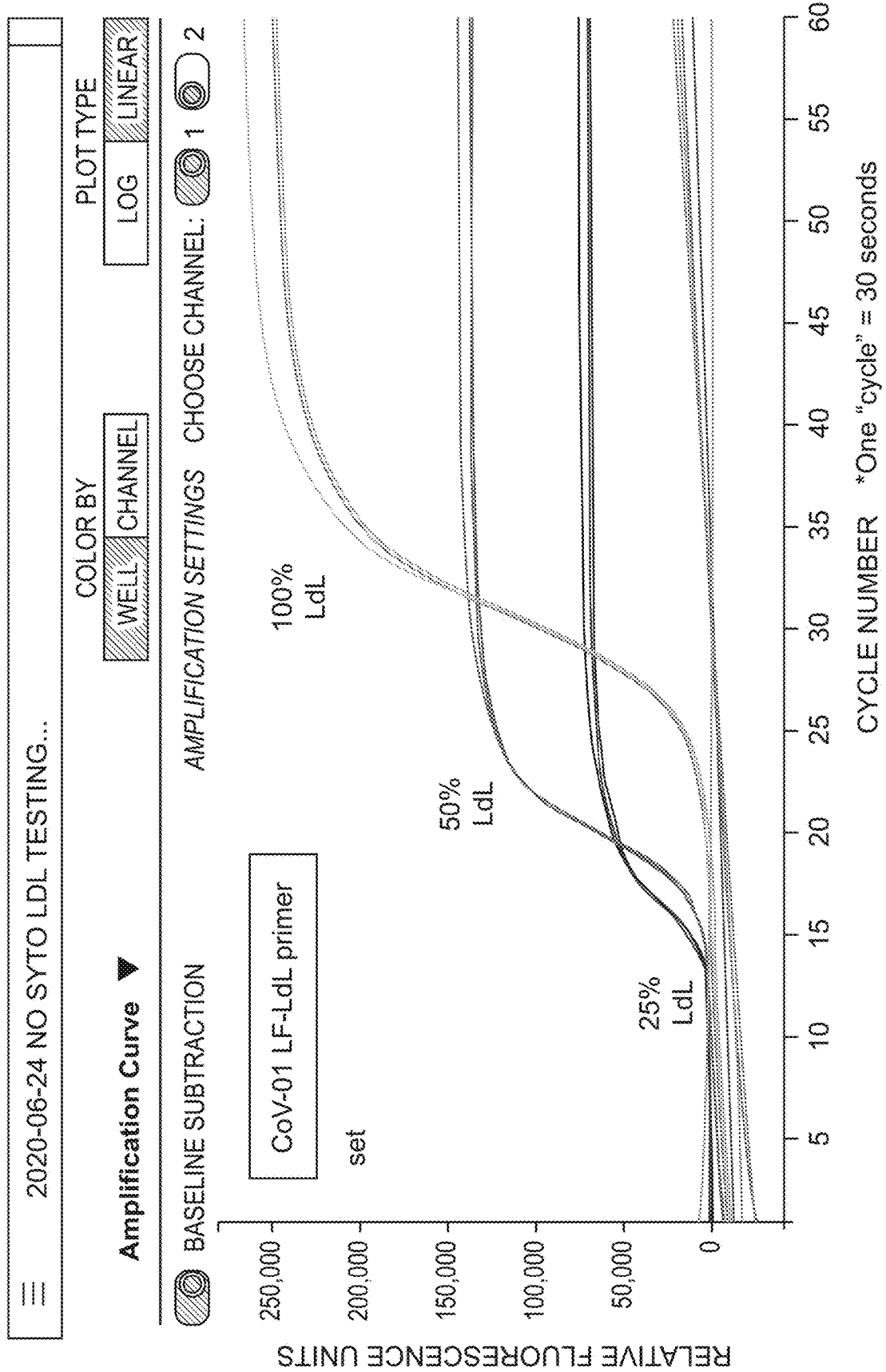
Figure 12:
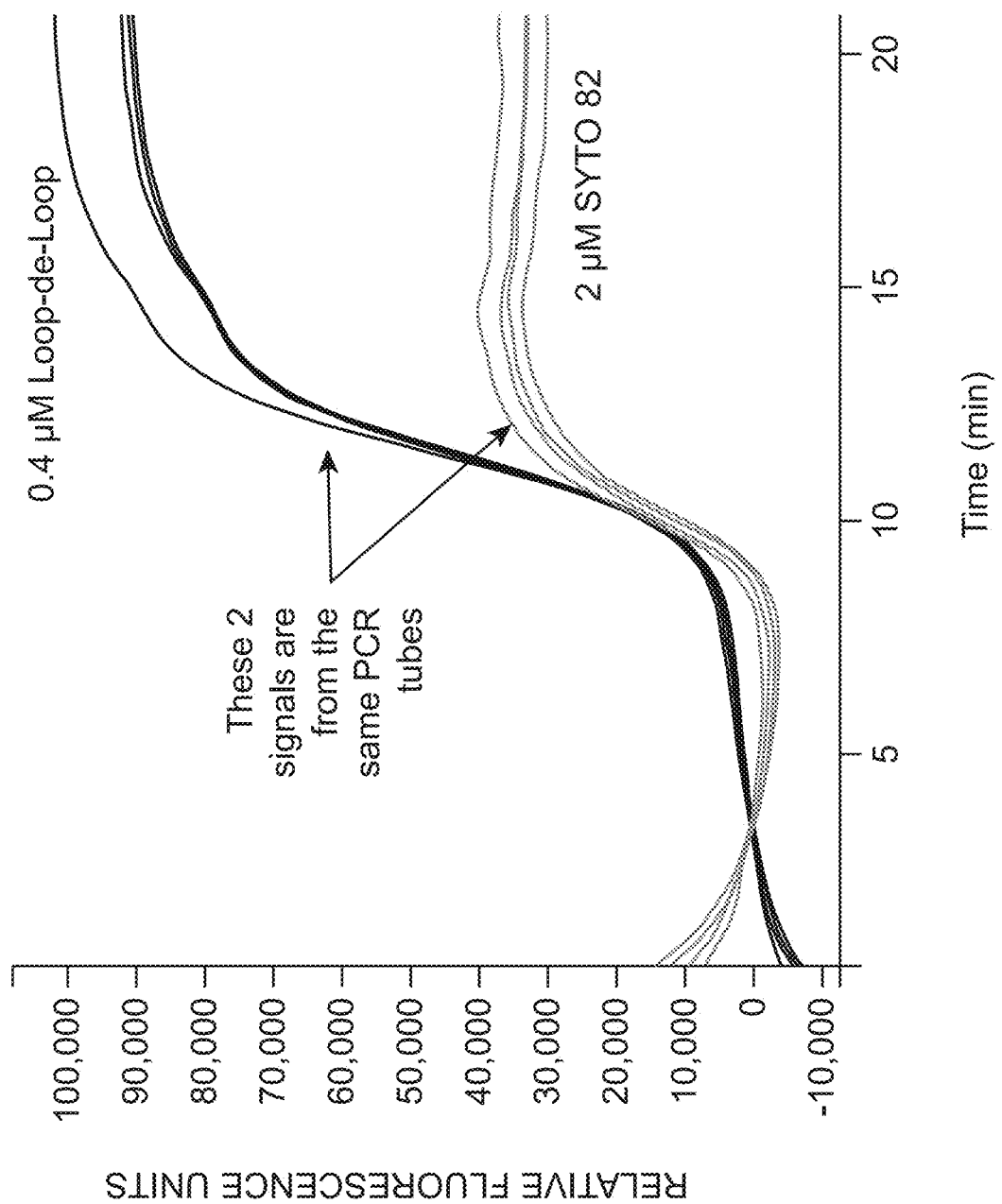
Figure 13A:
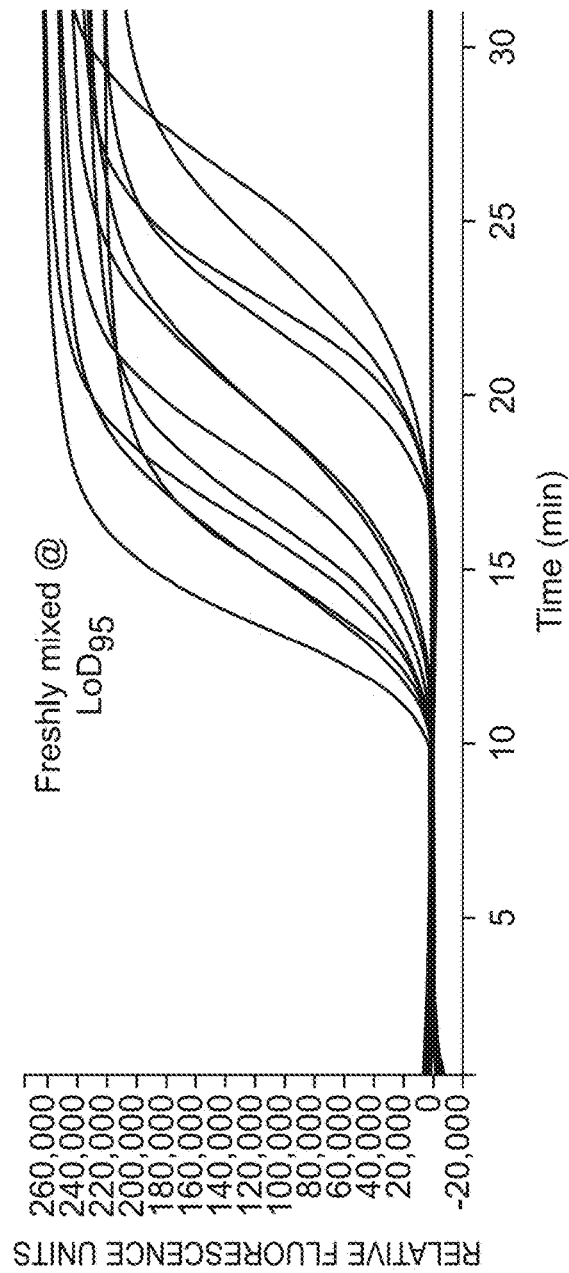
Figure 13B:
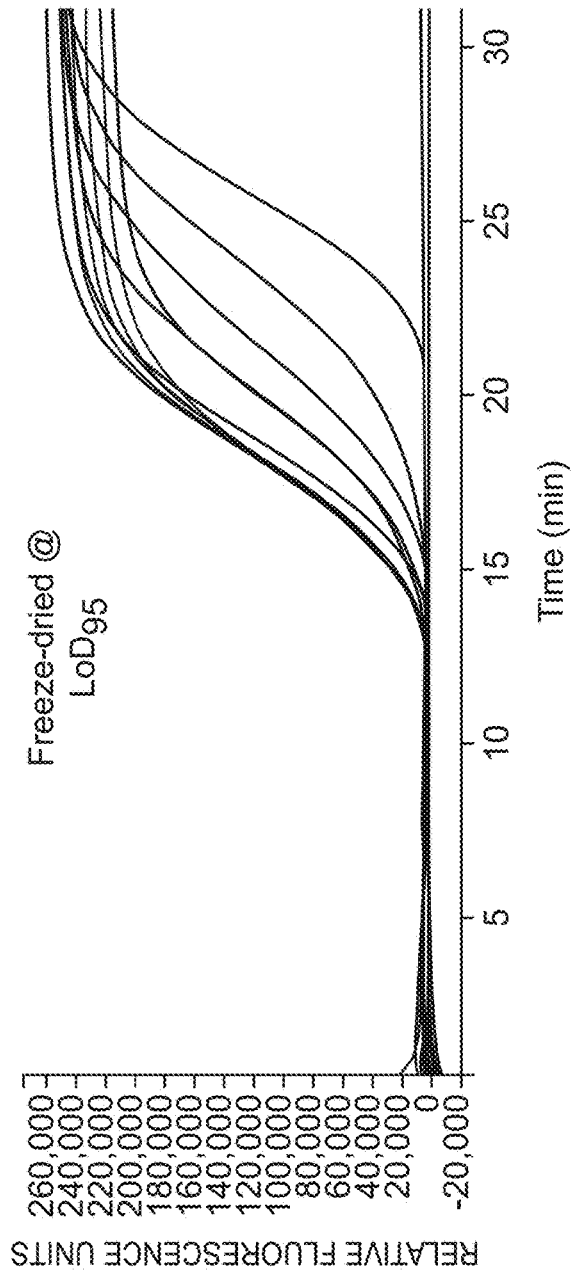

Loop-de-loop LAMP reaction mixtures were prepared as discussed above, one including ORF1ab primer set and the other including POP7b primer set. The ORF1ab primer set is specific to the SARS-CoV-2 virus, which has a single stranded positive sense RNA genome. The POP7b primer set is specific to a human RNA target that does not naturally occur as a DNA template; this primer set is therefore useful as a specific indicator of human RNA in a sample. In both cases, loop-de-loop was used to modify one of the 6 constituent primers used for LAMP to create a seventh looped primer. Looped primers utilized a fluorophore and quencher pair to generate an observable signal. For this experiment, moderately high concentrations of synthetic double stranded DNA templates, containing sequences on their positive sense strands that correspond to those of the RNA targets for each primer set, were utilized as the targets for LAMP reaction temperature optimization to minimize variability due to a reverse transcription step or stochastic noise encountered with dilute target. Target DNA dilutions were added to the mixtures within a 384-well plate. They were incubated at various temperatures ranging from 55 to 70° C., and the reaction was monitored via FAM fluorescence given off by the loop-de-loop primer. A real-time PCR machine was used to both heat the reactions and measure fluorescence in real-time. The reaction was run for 60 minutes. The experiment was done twice for overlapping temperature ranges (first test and second test) and the data are shown in FIGS. 9A and 9B. The figures depict time required to obtain enough signals for detection. The results show that the primer sets are active over a wide range of temperatures. For example, about 57-70° C. was an acceptable range for both the POP7b and ORF1ab primer sets. Optimal performance was achieved between 60° C. and 68° C.

Figure 14A:
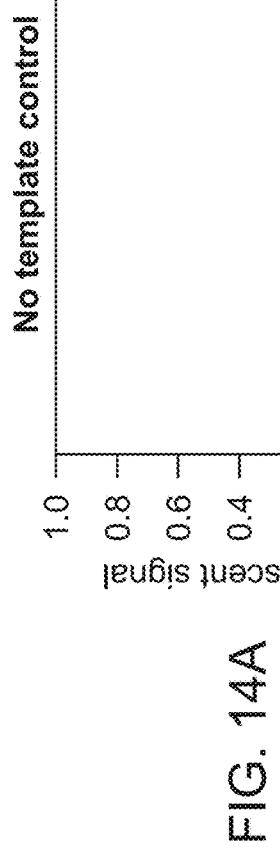
Figure 14C:
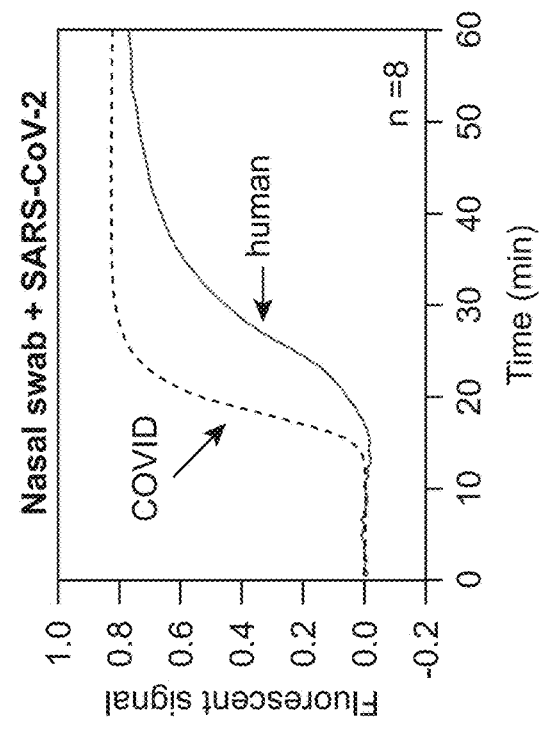
Figure 14B:
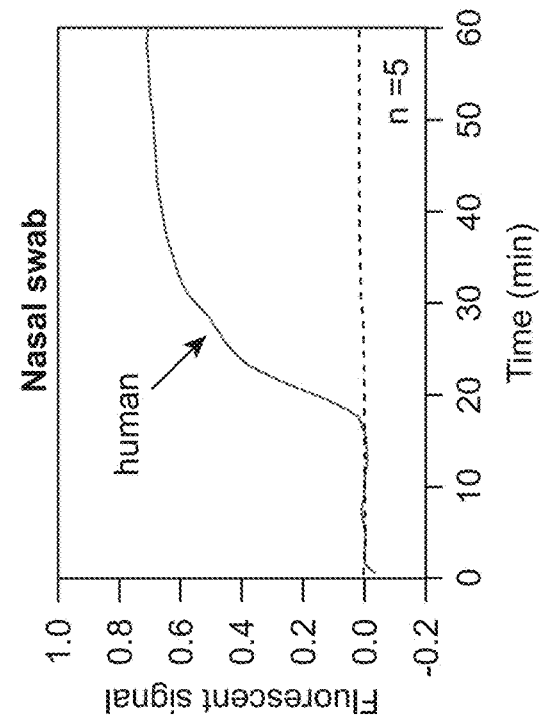
Figure 15B:
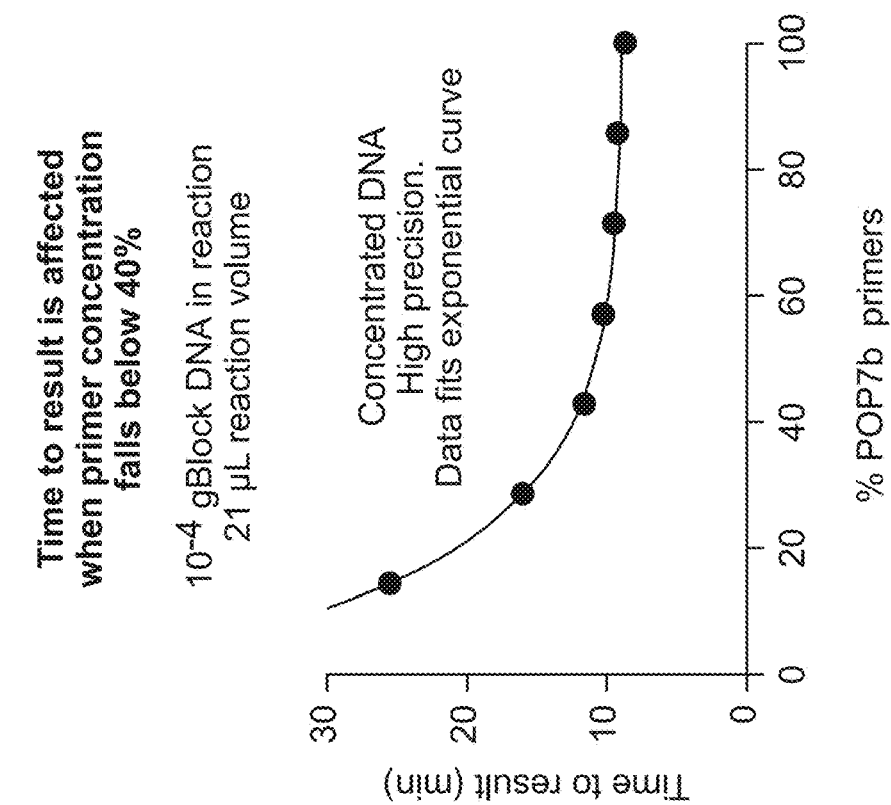
Figure 15A:
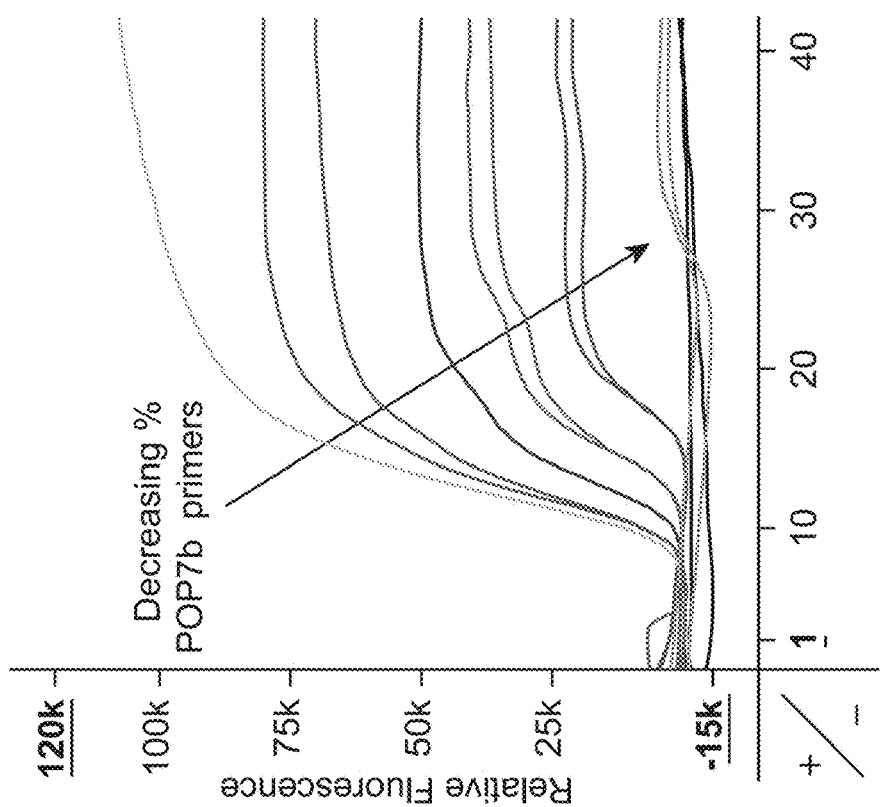

6.8.7. Example 7: Multiplexed Loop-De-Loop Reactions, to Detect Both Purified Targets and Targets in Crude Specimens FIGS. 14A, 14B and 14C show two fluorescent signals from loop-de-loop amplification of SARS-CoV-2 and human target sequences with ORF1ab and POP7b LdL primer sets, respectively. Signals from SARS-CoV-2 ORF1ab (FAM) and POP7b human internal control (Cy5) are shown. Three types of samples were used—a control sample without any target sequence (no template control) (FIG. 14A), human nasal swab (FIG. 14B) and human nasal swab combined with SARS-CoV-2 target sequence in the form of heat-inactivated virus (FIG. 14C). The human nasal swabs were self-collected from volunteers and added to the reactions directly without sample processing or nucleic acid extraction. Swabs were eluted into the reaction mixture by twisting for several seconds. The SARS-CoV-2 target sequence was introduced into the reactions as intact, heat-inactivated virus (ATCC VR-1986HK) spiked into SARS-CoV-2-positive reactions. ORF1ab LdL-FAM and POP7b LdL-Cy5 primer sets were duplexed at 1:1 ratios in replicate reaction volumes. Both primer sets utilized LdL primers at a 1:3 ratio relative to unlabeled primer analogues (25% strength). Reactions contained a reverse transcriptase, strand displacing polymerase, and RNase inhibitor. A real-time PCR machine (Bio-Rad CFX-384®) was used to incubate the reactions at 55.6 degrees Celsius for 2.5 minutes and then incubate reactions at 63.5 degrees Celsius for 60 minutes while recording fluorescence measurements for FAM and Cy5. As expected, no template control replicates showed no loop-de-loop fluorescence signals over 60 minutes. Reactions containing COVID-19-negative nasal swab samples showed amplification of the POP7b signal, as evidenced by an increase in Cy5 fluorescence, while ORF1ab signal remained flat (negative). Samples spiked with heat-inactivated virus showed spectrally duplexed detection of both RNA targets in single reaction vessels. The results show that loop-de-loop RT-LAMP permits single-tube spectral multiplexing of SARS-CoV-2 and human targets.

Multiplexed loop-de-loop testing for SARS-CoV-2 with the ORF1ab LdL primer set was as sensitive as PCR testing and did not require extraction, because reaction with a crude sample provided good results as provided in the below table. POP7b LdL primer set was used as an internal control. Serial dilutions of intact, heat-inactivated SARS-CoV-2 virus (ATCC VR-1986HK) were added to duplexed loop-de-loop reactions and monitored for real-time signal development. The limit of detection for the assay was estimated as LoD95=400 cp/swab=2.7×10$^3$ cp/mL for the specific format of the test kit.

| copies/reaction or copies/swab | Positive/ Total |
|---|---|
| 512 | 2/2 |
| 372 | 7/8 |
| 256 | 1/2 |
| 128 | 0/2 |

Triplexed loop-de-loop reaction was also tested in a single tube. It showed specific amplification of three targets, maintaining fast time to results. 2 separate targets for SARS-CoV-2 viral RNA were detected using 2 loop-de-loop primer sets labeled with FAM fluorophores. A human internal control loop-de-loop primer set labeled with Cy5 detected the third RNA target. The internal Cy5 fluorophore was paired with a 5' Iowa Black® RQ quencher. Reactions contained crude nasal swab eluate and were spiked with heat-inactivated SARS-CoV-2.

Additional looped primers were also tested for use in loop-de-loop primer sets for the POP7b human internal control. In one case, an internal TAMRA fluorophore, the second sensor molecule, was paired with a 5' Iowa Black® FQ quencher, the first sensor molecule. In another case a 5' Yakima Yellow® (Epoch Biosciences), the first sensor molecule, was paired with an internal Zen™ (Integrated DNA Technologies) quencher, the second sensor molecule. For the Yakima Yellow and Zen configuration, three variations of the looped primer were produced and tested. In the first variation, the first clamping oligonucleotide and the second clamping oligonucleotide were perfectly complementary and each was 6 bases long. The spacing oligonucleotide was 13 bases long. In the second variation, the first clamping oligonucleotide featured an additional base at its 5' end, so that the first clamping oligonucleotide was 7 bases long and the second clamping oligonucleotide was 6 bases long. There were 6 complementary bases between the first and second clamping oligonucleotides. The spacing oligonucleotide was 13 bases long. In the third variation, the first and second clamping oligonucleotides were both 7 bases long, and sequences were perfectly complementary. The spacing oligonucleotide was 10 bases long.

These additional looped primers are used for LAMP reactions. The reaction provides specific amplification signals of the target sequence.

6.8.8. Example 8: Detection of SARS-CoV-2 in Human Samples by Loop-De-Loop Amplification Loop-de-loop LAMP reaction mixtures were prepared to detect SARS-CoV-2 from unprocessed human saliva. Reactions were prepared in PCR tubes by rehydrating a lyophilized enzyme, dNTP, and oligonucleotide primer mixtures with a 10% vol/vol mixture of human saliva in a pH buffered salt solution. Lyophilized primer mixtures included primer sets for SARS-CoV-2 and a human internal control RNA sequence. Once rehydrated with saliva sample, reactions were incubated for a defined period of time at a preheat temperature to encourage viral lysis, RNase inhibition, and reverse transcription, and then incubated at a higher reaction temperature for LAMP DNA amplification. Temperature control and real-time fluorescence data were collected using a custom instrument.

Heat inactivated SARS-CoV-2 was added to a pool of fresh saliva collected from anonymous donors. 3-fold serial dilutions in saliva were prepared. 20 samples were tested using the loop-de-loop amplification methods. The read outs by the mobile app, eye, or real-time curve-inspection are summarized below. The results show that LoD is about 2,500 cp/mL.

| Whole virus (genome copies/ mL saliva) | Positive detections by mobile app | Positive by eye (turbidity) | Positive by real-time curve inspection |
|---|---|---|---|
| $1.77 \times 10^6$ cp/mL | 3/3 | 3/3 | 3/3 |
| $5.90 \times 10^5$ cp/mL | 3/3 | 3/3 | 3/3 |
| $1.97 \times 10^5$ cp/mL | 3/3 | 3/3 | 3/3 |
| $6.56 \times 10^4$ cp/mL | 23/23 | 23/23 | 23/23 |
| $2.19 \times 10^4$ cp/mL | 2/3 | 2/3 | 2/3 |
| 0 cp/mL (negative saliva) | 0 | 0 | 0 |

Figure 16:
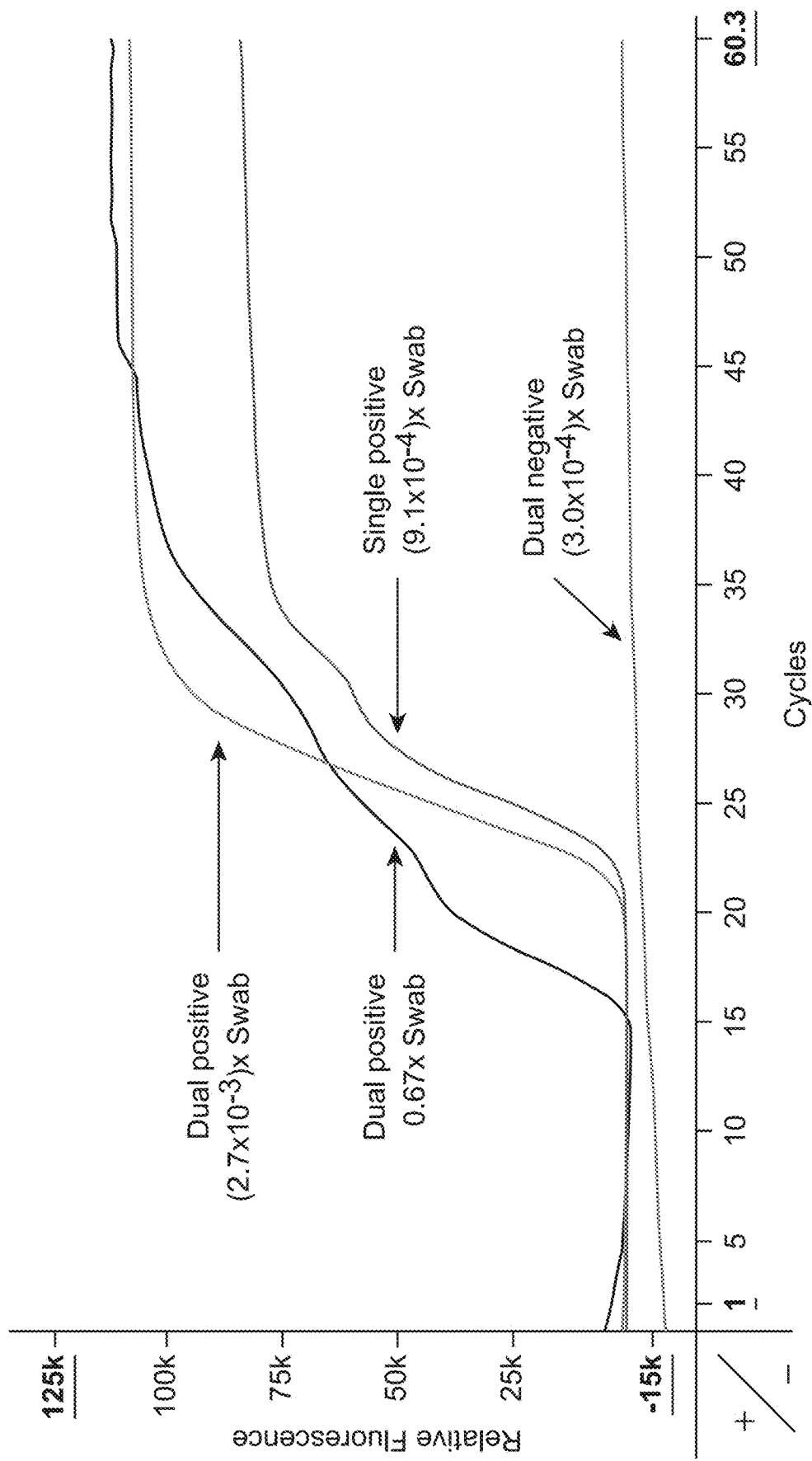

Self-collected nasal swab was obtained from a volunteer subject and added directly to the reaction mixture by twisting 10 times. FIG. 16 shows the amplification results from a nasal swab obtained from a symptomatic volunteer who was later confirmed to be positive for COVID by a PCR test. Results from positive/negative control samples are also provided. The results show that the sample (1× swab) was 365 times more concentrated than necessary to detect a positive sample with the loop-de-loop assay. Since LoD is presumed to be about 2,500 cp/mL, the particular sample was estimated to contain about $9.1 \times 10^5$ cp/mL of SARS-CoV-2 viral RNA.

Figure 17:
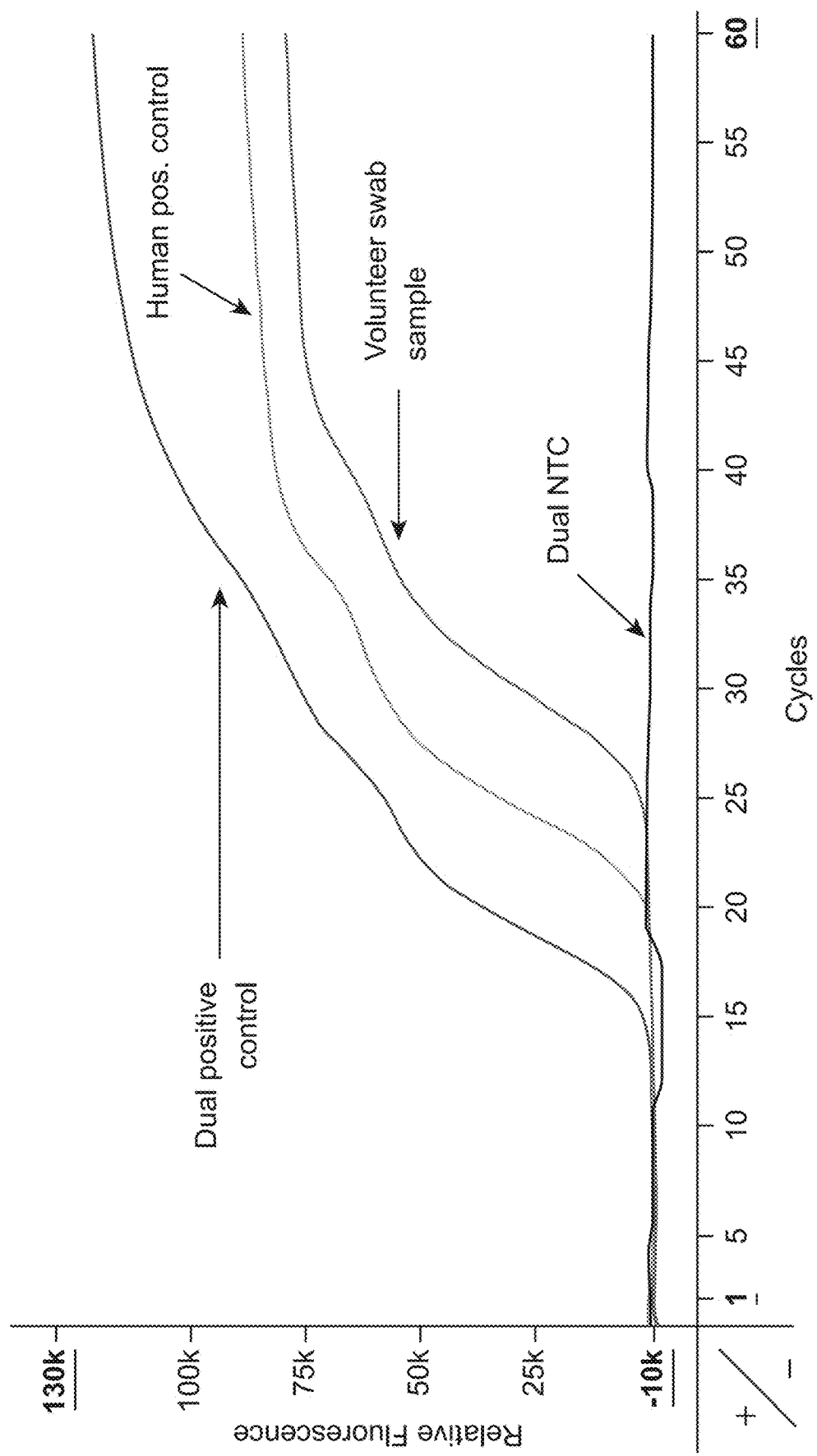

FIG. 17 shows the amplification results from a nasal swab obtained from a negative volunteer. The patient was detected negative both by the loop-de-loop reaction and PCR test.

Figure 18:
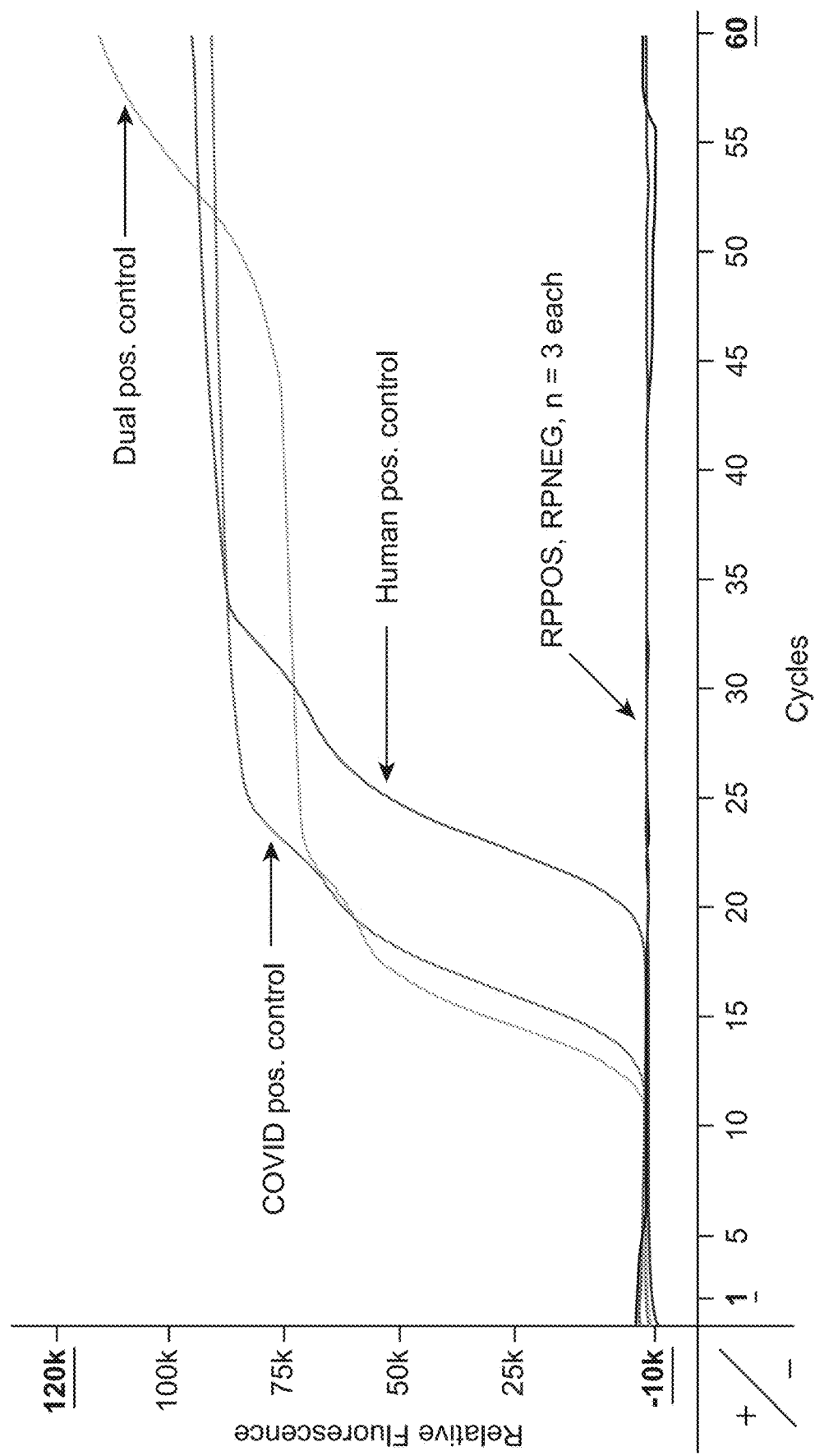

The reaction mixtures for detecting SARS-CoV-2 were multiplexed with primers for detecting a human genomic sequence at 1:1 ratio. The multiplexed amplification results are provided in FIG. 18. The results show specific and sensitive detection of two target sequences, without cross reactivity.

6.8.9. Example 9: Detection of *Chlamydia trachomatis* and *Neisseria gonorrhoeae* in Human Samples by Loop-De-Loop Amplification Three vaginal swabs (BD BBL Culture Swabs, a polyurethane foam tipped swab purchased from Lee Biosolutions, MO, sourced from unique individual donors) were eluted into 1,294 µL of rehydration buffer (431 µL per swab) using a 30 sec, 1 Hz twirl method (Panpradist et al., 2016). After loss of some fluid to the swabs, 1095 µL of pooled vaginal swab eluate was obtained. Fluid recovery was 85%. This swab eluate was pipetted into injection molded prototype disposables containing lyophilized reaction mixtures for Loop-de-Loop LAMP (one for Ct, one for Ng, and one for a human process control).

Each reaction was rehydrated with:
18 µL of swab eluate (swab twirled into rehydration buffer);
1 µL of whole Ct pathogen suspended in rehydration buffer
1 µL of whole Ng pathogen suspended in rehydration buffer Ct and Ng pathogen samples were in each reaction chamber of the disposables. So, for example, the Ct assay was tasked with detecting Ct in the simultaneous presence of Ng and human targets, as well as whatever bacterial milieu existed in the swab samples.

Figure 19:
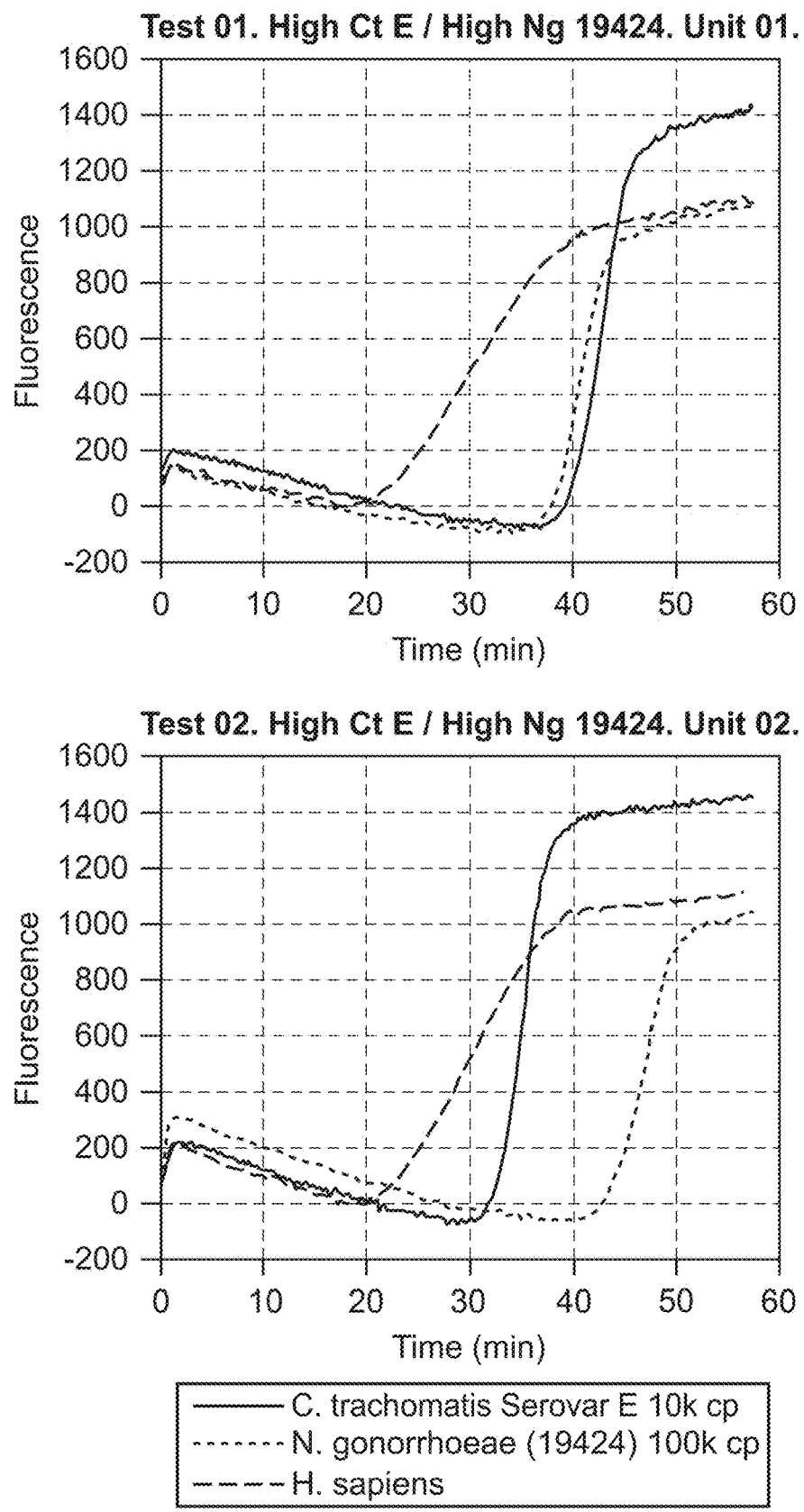
FIG. 19 shows fluorescent signals from loop-de-loop amplification of samples containing high *C. trachomatis* (Ct) (10,000 copies equivalent per reaction) and high *N. gonorrhoeae* (Ng) (10,000 copies equivalent per reaction).
Figure 19:
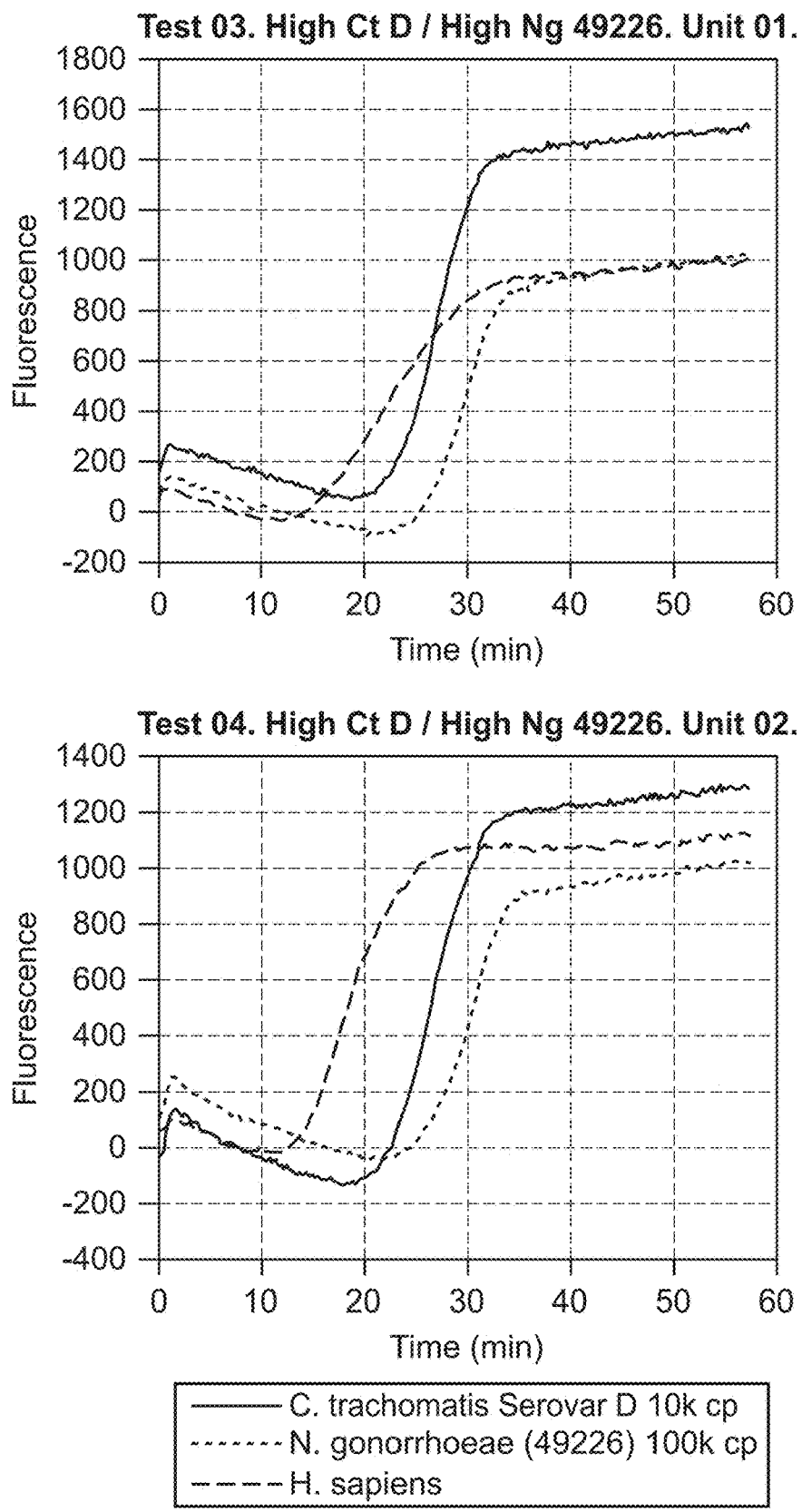
Figure 20:
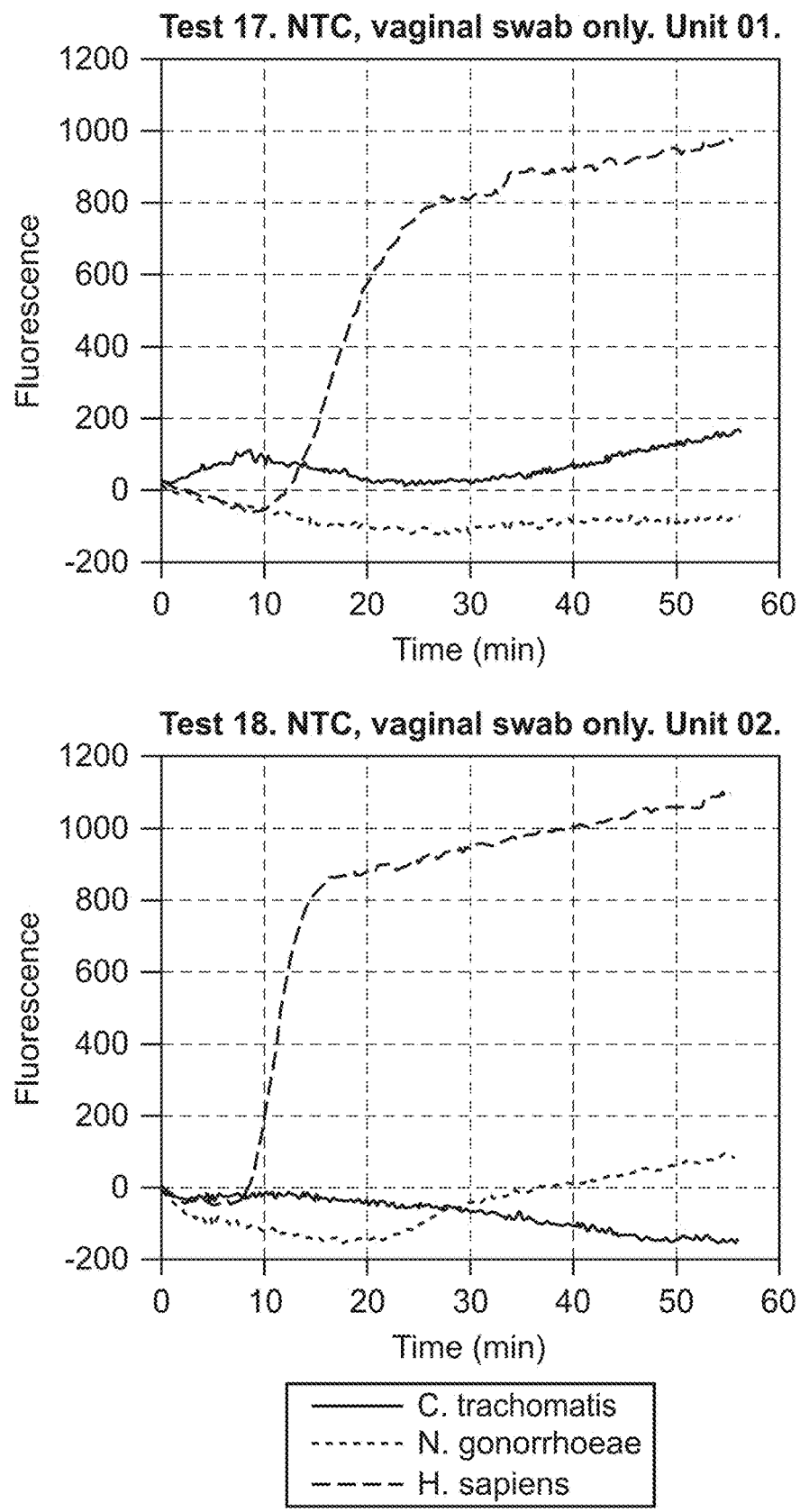
FIG. 20 shows fluorescent signals from loop-de-loop amplification of negative controls—swab only controls (left two panels) or buffer only controls (right two panels).
Figure 20:
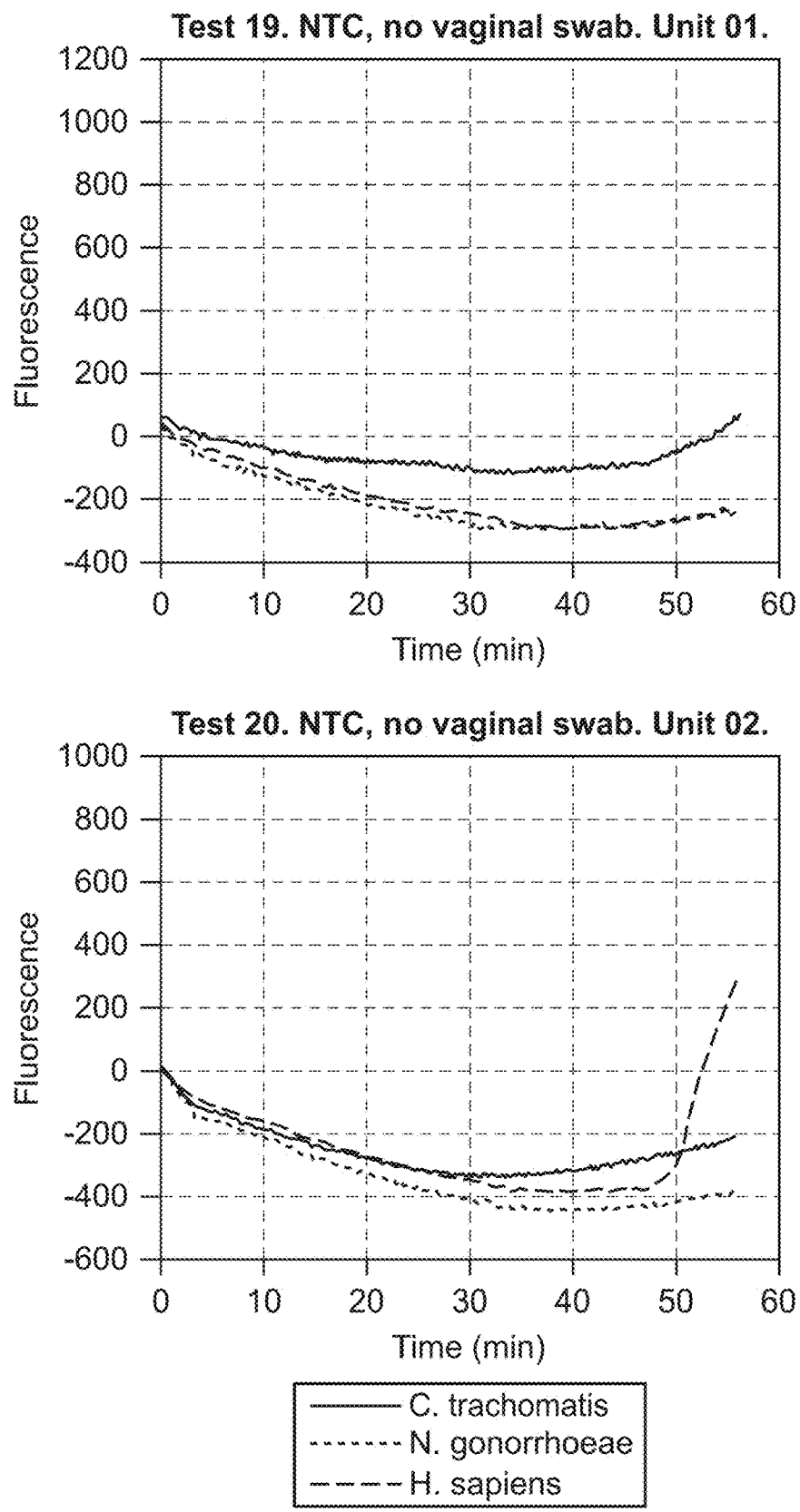

The amplification results are provided in FIGS. 19-22. FIG. 19 shows fluorescent signals from samples containing high Ct (10,000 copies equivalent per reaction) and high Ng (10,000 copies equivalent per reaction). FIG. 20 shows signals from negative controls—swab only controls (left two panels) or buffer only controls (right two panels). There was no Ct or Ng amplification in swab only controls, but a human genome sequence was amplified as expected. In the buffer only controls, there was no Ct or Ng amplification. *H. sapiens* amplification was detected late in one buffer only reaction (Test 20), likely from spurious amplification given the delayed signal.

These results show that the assay was sensitive to detect Ct at about 100 copies per reaction and Ng at about >1,000 copies per reaction.

| | | SEQUENCE | |
|---|---|---|---|
| | | Name | Sequence |
| SEQ ID NO: | 1 | Ng F3 | CCATTGATCCTTGGGACAG |
| SEQ ID NO: | 2 | Ng B3 | CAGACCGGCATAATACACAT |
| SEQ ID NO: | 3 | Ng FIP | GGGAATCGTAACGCACGGAAATAATGTGGCTTCGCAATTG |
| SEQ ID NO: | 4 | Ng BIP | AGCGGCAGCATTCAATTTGTTCCTGATTACTTTCCAGCGTG |

| | Name | Sequence |
|---|---|---|
| SEQ ID NO: 5 | Ng BIP-LdL | /5IABkFQ/GCAGGC ATATATATATATA GCCTGC/i6-FAMK/AGCGGCAGCATTCAATTTGTTCCTGATTACTTTCCAGCGTG |
| SEQ ID NO: 6 | Ng LF | ATACCGTCGTGGCGTTTG |
| SEQ ID NO: 7 | Ng LF-LdL | /5IABkFQ/GCAGGC ATATATATATATA GCCTGC/i6-FAMK/ATACCGTCGTGGCGTTTG |
| SEQ ID NO: 8 | Ng LB | CGCCTATACGCCTGCTAC |
| SEQ ID NO: 9 | Ct F3 | AATATCATCTTTGCGGTTGC |
| SEQ ID NO: 10 | Ct B3 | TCTACAAGAGTACATCGGTCA |
| SEQ ID NO: 11 | Ct FIP | TCGAGCAACCGCTGTGACGACCTTCATTATGTCGGAGTC |
| SEQ ID NO: 12 | Ct BIP | GCAGCTTGTAGTCCTGCTTGAGTCTTCGTAACTCGCTCC |
| SEQ ID NO: 13 | Ct LF | TACAAACGCCTAGGGTGC |
| SEQ ID NO: 14 | Ct LB | CGGGCGATTTGCCTTAAC |
| SEQ ID NO: 15 | Ct LF-LdL | /5IABkFQ/GCAGGC ATATATATATATA GCCTGC/i6-FAMK/ACAAACGCCTAGGGTGC |
| SEQ ID NO: 16 | Hs_F3 | TCCCTTGTACGCTCGATCT |
| SEQ ID NO: 17 | Hs B3 | AGTCCTGGGAAGGGAGAC |
| SEQ ID NO: 18 | Hs FIP | TGGTCCTCACTGGGGTCACCGAGCTGTGGGCAGAAAACG |
| SEQ ID NO: 19 | Hs BIP | GCCCGGGGATTCTGGAAATTGTGTCCCAGCTTGATCTCACC |
| SEQ ID NO: 20 | Hs LF | GTGGCCTGTGACACCAGAT |
| SEQ ID NO: 21 | Hs LB | TTGGCCCCATGATTCCTCAGT |
| SEQ ID NO: 22 | Hs LF-LdL | /5IABkFQ/GCAGGCATATATATATATAGCCTGC/i6-FAMK/GTGGCCTGTGACACCAGAT |

8. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

9. EQUIVALENTS

While various specific embodiments have been illustrated and described, the above specification is not restrictive. It will be appreciated that various changes can be made without departing from the spirit and scope of the invention(s). Many variations will become apparent to those skilled in the art upon review of this specification.

What is claimed is:

1. A looped primer for loop-de-loop amplification (LdL) of a target sequence, comprising from 5' to 3':
   a first sensor molecule;
   a first clamping oligonucleotide;
   a spacing oligonucleotide;
   a second clamping oligonucleotide,
      wherein the first clamping oligonucleotide, the spacing oligonucleotide and the second clamping oligonucleotide can form a hairpin structure at a temperature below the melting temperature ($T_m$) of the first and second clamping oligonucleotides;
   a second sensor molecule,
      wherein the first sensor molecule and the second sensor molecule are a first biosensor pair; and
   a first primer sequence complementary to a first binding site on the target sequence; and
   further comprising at least a first additional oligonucleotide, wherein the first additional oligonucleotide is at 5' end of the looped primer.

2. The looped primer of claim 1, wherein the second clamping oligonucleotide is complementary to the first clamping oligonucleotide.

3. The looped primer of claim 1, wherein the first biosensor pair is an energy donor and acceptor pair.

4. The looped primer of claim 3, wherein the first biosensor pair is an energy donor and acceptor pair for fluorescence resonance energy transfer (FRET) or bioluminescence resonance energy transfer (BRET).

5. The looped primer of claim 1, wherein the first sensor molecule and the second sensor molecule can form a complex that generates a detectable light signal.

6. The looped primer of claim 1, wherein the melting temperature ($T_m$) of the first and second clamping oligonucleotides is above 60° C.

7. The looped primer of claim 6, wherein the melting temperature ($T_m$) of the first and second clamping oligonucleotides is above 70° C.

8. The looped primer of claim 7, wherein the melting temperature ($T_m$) of the first and second clamping oligonucleotides is above 80° C.

9. The looped primer of claim 6, wherein the melting temperature ($T_m$) of the first and second clamping oligonucleotides is from 70 to 80° C.

10. The looped primer of claim 1, wherein the melting temperature ($T_m$) of the first and second clamping oligonucleotides is below 60° C.

11. The looped primer of claim 1, wherein each of the first clamping oligonucleotide and the second clamping oligonucleotide is from 3 to 10-nucleotides long.

12. The looped primer of claim 1, wherein the spacing oligonucleotide is from 5 to 35-nucleotides long.

13. The looped primer of claim 1, wherein the first clamping oligonucleotide, the spacing oligonucleotide, and the second clamping oligonucleotide together are from 15 to 35-nucleotides long.

14. The looped primer of claim 1, wherein the first clamping oligonucleotide, the spacing oligonucleotide, and the second clamping oligonucleotide comprise (i) a nucleobase selected from adenine, guanine, cytosine, thymine, and uracil, (ii) a locked nucleic acid, (iii) a 2' O-methyl RNA base, (iv) a phosphorothioated DNA base, (v) a phosphorothioated RNA base, (vi) a phosphorothioated 2'-O-methyl RNA base, or (vii) a combination thereof.

15. The looped primer of claim 1, further comprising a second additional oligonucleotide, wherein the second additional oligonucleotide is between the first sensor molecule and the first clamping oligonucleotide.

16. The looped primer of claim 1, wherein the first additional oligonucleotide is a barcode sequence.

17. The looped primer of claim 1, wherein the target sequence is specific to a pathogen genome.

18. The looped primer of claim 17, wherein the pathogen is *Neisseria gonorrhoeae*, or SARS-CoV-2.

19. A primer mixture for loop-de-loop amplification of a target sequence, comprising the looped primer of claim 1.

20. The primer mixture of claim 19, further comprising (i) a forward inner primer (FIP), (ii) a backward inner primer (BIP), (iii) a forward primer (F3), and a backward primer (B3), wherein the FIP, the BIP, the F3, and the B3 bind to six different binding sites on the target sequence.

21. The primer mixture of claim 20, further comprising (i) a loop forward primer (LF) and (ii) a loop backward primer (LB), wherein the LF and the LB bind to two different binding sites on the target sequence.

22. The primer mixture of claim 19, further comprising a second looped primer, wherein the second looped primer comprises:
a third sensor molecule;
a third clamping oligonucleotide;
a second spacing oligonucleotide;
a fourth clamping oligonucleotide,
wherein the third clamping oligonucleotide, the second spacing oligonucleotide and the fourth clamping oligonucleotide can form a hairpin structure at a temperature below the melting temperature ($T_m$) of the third and fourth clamping oligonucleotides;
a fourth sensor molecule,
wherein the third sensor molecule and the fourth sensor molecule are a second biosensor pair, and the second biosensor pair differs from the first biosensor pair; and
a second primer sequence complementary to a first binding site on a second target sequence.

23. The primer mixture of claim 22, wherein the target sequence and the second target sequence are different.

24. The primer mixture of claim 22, further comprising (i) a second forward inner primer (SFIP), (ii) a second backward inner primer (SBIP), (iii) a second forward primer (SF3), and (iv) a second backward primer (SB3), wherein the SFIP, the SBIP, the SF3, and the SB3 bind to six different binding sites on the second target sequence.

25. The primer mixture of claim 22, further comprising (i) a second loop forward primer (SLF) and (ii) a second loop backward primer (SLB), wherein the SLF and the SLB bind to two different binding sites on the second target sequence.

26. The primer mixture of claim 22, further comprising a third looped primer, wherein the third looped primer comprises:
a fifth sensor molecule;
a fifth clamping oligonucleotide;
a third spacing oligonucleotide;
a sixth clamping oligonucleotide,
wherein the fifth clamping oligonucleotide, the third spacing oligonucleotide and the sixth clamping oligonucleotide can form a hairpin structure at a temperature below the melting temperature ($T_m$) of the fifth and sixth clamping oligonucleotides;
a sixth sensor molecule,
wherein the fifth sensor molecule and the sixth sensor molecule are a third biosensor pair, and the third biosensor pair differs from the first biosensor pair and the second biosensor pair; and
a second primer sequence complementary to a first binding site on a third target sequence.

27. A kit for loop-de-loop amplification of a target sequence, comprising the looped primer of claim 1 and polymerase.

28. The kit of claim 27, further comprising a reverse transcriptase.

29. The kit of claim 27, wherein the polymerase is a *Geobacillus stearothermophilus* polymerase.

* * * * *

SEQUENCE LISTING

```
<160> NUMBER OF SEQ ID NOS: 22

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccattgatcc ttgggacag                                               19
```

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cagaccggca taatacacat                                              20

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gggaatcgta acgcacggaa ataatgtggc ttcgcaattg                        40

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agcggcagca ttcaatttgt tcctgattac tttccagcgt g                      41

<210> SEQ ID NO 5
<211> LENGTH: 67
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcaggcatat atatatatag cctgctagcg gcagcattca atttgttcct gattactttc  60
cagcgtg                                                            67

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ataccgtcgt ggcgtttg                                                18

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcaggcatat atatatatag cctgctatac cgtcgtggcg tttg                   44

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgcctatacg cctgctac                                                   18

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aatatcatct ttgcggttgc                                                 20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tctacaagag tacatcggtc a                                               21

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcgagcaacc gctgtgacga ccttcattat gtcggagtc                            39

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcagcttgta gtcctgcttg agtcttcgta actcgctcc                            39

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tacaaacgcc tagggtgc                                                   18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgggcgattt gccttaac                                                   18

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcaggcatat atatatatag cctgctacaa acgcctaggg tgc                       43

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tcccttgtac gctcgatct                                                  19

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agtcctggga agggagac                                                   18

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tggtcctcac tggggtcacc gagctgtggg cagaaaacg                            39

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcccggggat tctggaaatt gtgtcccagc ttgatctcac c                         41

-continued

```
<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtggcctgtg acaccagat                                                19

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttggccccat gattcctcag t                                             21

<210> SEQ ID NO 22
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcaggcatat atatatatag cctgctgtgg cctgtgacac cagat                   45
```